(12) United States Patent
Boydston et al.

(10) Patent No.: US 8,604,098 B2
(45) Date of Patent: Dec. 10, 2013

(54) ON-DEMAND PHOTOINITIATED POLYMERIZATION

(75) Inventors: Andrew J. Boydston, Seattle, WA (US); Robert H. Grubbs, South Pasadena, CA (US); Chris Daeffler, Pasadena, CA (US); Nebojsa Momcilovic, Vienna, VA (US)

(73) Assignee: California Institute of Technology, Pasadena, CA (US)

( * ) Notice: Subject to any disclaimer, the term of this patent is extended or adjusted under 35 U.S.C. 154(b) by 21 days.

(21) Appl. No.: 13/177,483

(22) Filed: Jul. 6, 2011

(65) Prior Publication Data
US 2012/0035293 A1 Feb. 9, 2012

Related U.S. Application Data

(60) Provisional application No. 61/362,249, filed on Jul. 7, 2010.

(51) Int. Cl.
*C08F 283/12* (2006.01)
*C08F 2/46* (2006.01)
*C08J 3/28* (2006.01)

(52) U.S. Cl.
USPC .............................. 522/99; 522/148; 522/1

(58) Field of Classification Search
USPC ................................ 522/99, 148, 1
See application file for complete search history.

(56) References Cited

U.S. PATENT DOCUMENTS

| | | | |
|---|---|---|---|
| 6,824,266 B2 | 11/2004 | Jethmalani et al. | |
| 7,122,227 B2 * | 10/2006 | Vaughn-Spickers et al. | 428/1.1 |
| 7,892,711 B2 * | 2/2011 | Kondo et al. | 430/20 |
| 7,911,676 B2 * | 3/2011 | Knowles et al. | 359/288 |
| 7,955,665 B2 * | 6/2011 | Nishiyama et al. | 428/1.2 |
| 2006/0177605 A1 * | 8/2006 | Lub et al. | 428/1.3 |
| 2006/0193998 A1 | 8/2006 | Harding et al. | |
| 2007/0159594 A9 * | 7/2007 | Jani et al. | 351/160 R |
| 2008/0094326 A1 | 4/2008 | Yamaki et al. | |
| 2008/0137030 A1 | 6/2008 | Hoffman | |
| 2008/0171143 A1 | 7/2008 | Nishikawa et al. | |
| 2008/0199782 A1 | 8/2008 | Yoshizawa et al. | |
| 2010/0052196 A1 * | 3/2010 | Yasuda et al. | 264/1.34 |
| 2011/0198546 A1 * | 8/2011 | Choi | 252/586 |

FOREIGN PATENT DOCUMENTS

| | | | |
|---|---|---|---|
| JP | 2003-084242 | * | 3/2003 |
| WO | WO 2006/003893 | * | 1/2006 |
| WO | WO 2007/055316 | * | 5/2007 |
| WO | WO 2012/006370 A3 | | 1/2012 |

OTHER PUBLICATIONS

Jaume Garcia-Amoros, Kintetic study of the fast thermal cis-to-trans isomerization of para-, ortho- and polyhydroxyazobenzenes, 2010, Phys. Chem. Chem. Phys., 12, 13238-13242.*
Ronald A. Henry, Aryl Diazomorpholides, 1943, Journal of American Chemical Society, vol. 65, pp. 479-548.*

* cited by examiner

*Primary Examiner* — Ling Choi
*Assistant Examiner* — Jessica E Whiteley
(74) *Attorney, Agent, or Firm* — Woodcock Washburn, LLP

(57) ABSTRACT

Compositions and methods for adjustable lenses are provided. In some embodiments, the lenses contain a lens matrix material, a masking compound, and a prepolymer. The lens matrix material provides structure to the lens. The masking compound is capable of blocking polymerization or crosslinking of the prepolymer, until photoisomerization of the compound is triggered, and the compound is converted from a first isomer to a second isomer having a different absorption profile. The prepolymer is a composition that can undergo a polymerization or crosslinking reaction upon photoinitiation to alter one or more of the properties of the lenses.

40 Claims, 3 Drawing Sheets

ON-DEMAND PHOTOINITIATED POLYMERIZATION

CROSS REFERENCE TO RELATED APPLICATIONS

This application claims priority under 35 U.S.C. §119 to U.S. Provisional Application Ser. No. 61/362,249, filed Jul. 7, 2010, the contents of which is incorporated herein by reference in its entirety.

ACKNOWLEDGEMENT OF GOVERNMENT SUPPORT

This invention was made with U.S. Government support under Grant No. DE-FG02-05ER46218 awarded by the Department of Energy and Grant No. GM031332 awarded by the National Institutes of Health. The Government has certain rights in the invention.

BACKGROUND

The insertion of an intraocular lens is a common eye surgical procedure for the treatment of cataracts, or as a form of refractive surgery to change the eye's optical power and decrease or eliminate dependency on glasses or contact lenses. Successful refractive eye surgery can reduce or cure common vision disorders such as myopia, hyperopia and astigmatism.

For certain applications, healing alters the physical environment around the lens. Lens adjustment via photoinitiated polymerization can account for the changes in the physical environment. During the healing time, premature polymerization of the lens material (e.g. from exposure to sunlight) can be detrimental to the procedure.

As such, lenses and pre-polymer materials that resist polymerization in sunlight during healing but which can be readily polymerized on demand are of interest.

SUMMARY

Compositions for adjustable lenses are provided, and methods for making and modifying the same. In some embodiments, the lenses contain a lens matrix material, a masking compound, and a prepolymer. The lens matrix material provides structure to the lens. The masking compound is capable of blocking polymerization or crosslinking of the prepolymer, until photoisomerization of the compound is triggered, and the masking compound is converted from a first isomer to a second isomer having a different absorption profile. The prepolymer is a composition that can undergo a polymerization or crosslinking reaction upon photoinitiation, to alter one or more of the properties of the lenses.

In one aspect, the disclosure provides a method for modifying a composition including: (a) a triggering step, including applying electromagnetic energy of a first wavelength and intensity to the composition, where the triggering step causes photoisomerization of a masking compound in the composition; and (b) a polymerization or crosslinking step, including applying electromagnetic energy of a second wavelength and intensity to the composition, where the polymerization or crosslinking step causes polymerization or crosslinking of a prepolymer in the composition.

In some embodiments, the first and second wavelengths are between 1 and 800 nm, and where the electromagnetic energy of the second wavelength is optionally generated from a monochromatic source.

In some embodiments, photoisomerization converts the masking compound from a first isomer to a second isomer, where the second isomer absorbs less light at the second wavelength compared with the first isomer. In some embodiments, photoisomerization is selected from a cis-trans, cyclization, or ring-opening transition. In some embodiments, the masking compound includes a —C═C— or —N═N— moiety that undergoes a cis-trans transition. In some embodiments, the masking compound undergoes a cyclization or ring-opening photoisomerization upon absorption of electromagnetic energy at the first wavelength.

In some embodiments, the electromagnetic energy at the second wavelength induces polymerization by direct initiation of the prepolymer. In some embodiments, the electromagnetic energy at the second wavelength induces polymerization indirectly on the prepolymer via activation of a photoinitiator. In some embodiments, the electromagnetic energy at the second wavelength induces crosslinking of the prepolymer via a cross-linkable monomer or oligomer.

In some embodiments, the subject method further includes: (c) waiting for a period of time sufficient to allow the masking compound to isomerize from the second isomer to the first isomer; and (d) repeating the triggering step and the polymerization or crosslinking step.

In some embodiments, the composition is an intraocular implant and the polymerization or crosslinking step modifies an optical property of the implant.

In another aspect, the disclosure provides a composition including: (a) a masking compound capable of photoisomerization between a first isomer and a second isomer upon absorption of electromagnetic energy at a first wavelength and intensity; and (b) a prepolymer capable of polymerization upon photoinitiation with electromagnetic energy at a second wavelength and intensity.

In some embodiments, the first isomer of the masking compound absorbs more light at the second wavelength than the second isomer of the masking compound. In some embodiments, the first isomer of the masking compound is capable of blocking photoinitiation of the prepolymer upon application of ambient sunlight. In some embodiments, the prepolymer is capable of polymerization upon photoinitiation with electromagnetic energy at the second wavelength and intensity in the presence of the second isomer of the masking compound. Thus, in some embodiments, the disclosure provides compositions including the prepolymer and the masking compound, wherein the masking compound is present in sufficient quantity to prevent polymerization or crosslinking of the prepolymer upon exposure to ambient sunlight, and wherein isomerization of a sufficient proportion of the masking compound (to the second isomer, e.g. by application of light at the first wavelength described herein) reduces the inhibitory effect of the masking compound to the extent that the prepolymer can polymerize or crosslink (e.g. upon application of light at the second wavelength described herein).

In some embodiments, the prepolymer includes a photocrosslinker or a photoinitiator. In some embodiments, the photocrosslinker or photoinitiator has an absorption maximum (i.e. a wavelength that causes the photocrosslinker or photoinitiator to initiate crosslinking or polymerization of a prepolymer) that is about 50 nm or less (e.g., about 40 nm or less, about 30 nm or less, about 20 nm or less, or about 10 nm or less) from a region of substantial absorption (e.g., an absorption maximum) in the absorption spectrum of the first isomer of the masking compound. In some embodiments, the photocrosslinker or photoinitiator has an absorption maximum that is closer to the absorption maximum of the first isomer as compared to the second isomer of the masking compound.

In some embodiments, the subject composition is an intraocular implant further including a matrix material.

In another aspect, the disclosure provides a method for implanting an intraocular implant including: (a) inserting the intraocular implant into the eye of a patient; (b) allowing the eye to heal for a period of time; (c) applying electromagnetic energy of a first wavelength and intensity to the intraocular implant to cause photoisomerization of a masking compound; and (d) applying electromagnetic energy of a second wavelength and intensity to the intraocular implant to cause polymerization of a prepolymer.

In some embodiments, the intraocular implant is a composition including: (a) a masking compound capable of photoisomerization between a first isomer and a second isomer upon absorption of electromagnetic energy at a first wavelength and intensity; (b) a prepolymer capable of polymerization upon photoinitiation with electromagnetic energy at a second wavelength and intensity; and (c) a matrix material.

In some embodiments, the first wavelength is between about 1 and about 800 nm, such as between about 200 and about 800 nm, between about 250 and about 600 nm, between about 300 and about 400 nm, between about 340 and about 365 nm (e.g., about 365 nm), or between about 340 and about 350 nm. For example, the first wavelength is less than 800 nm, or less than 600 nm, or less than 400 nm, or less than 365 nm. Also for example, the first wavelength is greater than 1 nm, or greater than 200 nm, or greater than 250 nm, or greater than 300 nm, or greater than 340 nm. In some embodiments, the second wavelength is between about 1 and about 800 nm, such as between 200 and 800 nm, between about 300 and about 650 nm, between about 300 and about 500 nm, between about 300 and about 400 nm, between about 340 and about 370 nm (e.g., about 365 nm), or between about 340 and about 350 nm. For example, the second wavelength is less than 800 nm, or less than 600 nm, or less than 400 nm, or less than 365 nm. Also for example, the second wavelength is greater than 1 nm, or greater than 200 nm, or greater than 250 nm, or greater than 300 nm, or greater than 340 nm. In some embodiments, the first and the second wavelengths are the same. In some embodiments, in the subject methods, the steps of applying electromagnetic energy of the first and second wavelengths are performed concurrently, e.g., substantially at the same time. In some embodiments, the electromagnetic energy of the first and second wavelengths is applied from the same light source.

In some embodiments, the subject method further includes repeating (c) and (d).

In another aspect, the disclosure provides a method for making an intraocular implant, the method including combining: (a) a lens matrix material; (b) a masking compound capable of photoisomerization between a first isomer and a second isomer upon absorption of electromagnetic energy at a first wavelength and intensity; and (c) a prepolymer capable of polymerization or crosslinking upon photoinitiation with electromagnetic energy at a second wavelength and intensity.

In some embodiments, the lens matrix material includes a polymer selected from a polyacrylate, a polymethacrylate, a silicone, and a polysiloxane.

In some embodiments, the prepolymer includes a crosslinkable monomer or oligomer and an optional crosslinking moiety.

In some embodiments, the prepolymer includes a photoinitiator and a polymerizable moiety.

In another aspect, the disclosure provides masking compounds for use in the subject methods and compositions, as summarized above and described herein.

In some embodiments, the masking compound is described by the structure of formula (I):

$(Z^1)_{n1}$—Y—$(Z^2)_{n2}$     (I)

where Y is a photoisomerizable moiety;
$n^1$ and $n^2$ are each independently 0, 1, 2 or 3; and
each $Z^1$ and $Z^2$ is independently a polymerizable moiety or a crosslinking moiety that is connected to Y via an optional linker.

In some embodiments, in formula (I), $n^1$ is 2 or 3, and each $Z^1$ is attached to Y via a branched linker (e.g., an amino or an ammonium containing linker). In some embodiments, in formula (I), $n^2$ is 2 or 3, and each $Z^2$ is attached to Y via a branched linker (e.g., an amino or an ammonium containing linker). In some embodiments, in formula (I), when $n^1$ and/or $n^2$ is 2 or 3, then each $Z^1$ and/or $Z^2$ is independently connected to Y via a linear linker that is not branched.

In some embodiments, the masking compound is described by the structure of formula (II):

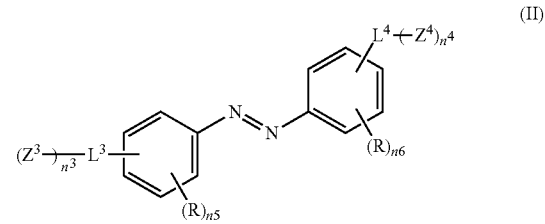

where:
$n^5$ and $n^6$ are each independently 0, 1, 2, 3, 4 or 5;
each R is independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide; and
$(Z^3)_{n3}$-$L^3$- and -$L^4$-$(Z^4)_{n4}$ may be independently absent or present, and when present;
$n^3$ and $n^4$ are each independently 1, 2 or 3;
each $Z^3$ and $Z^4$ is independently a polymerizable moiety or a crosslinking moiety; and
$L^3$ and $L^4$ are linkers.

In some embodiments, the masking compound is described by the structure of formula (III):

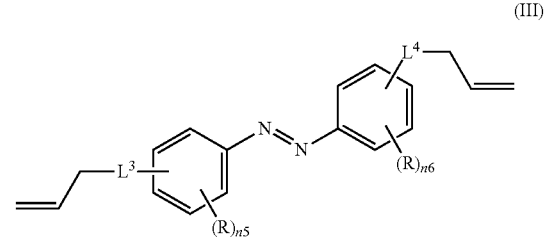

where $L^3$ and $L^4$ are linkers;
$n^5$ and $n^6$ are each independently 0, 1, 2, 3 or 4; and
each R is independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide.

In some embodiments, the masking compound is described by one of the following structures:

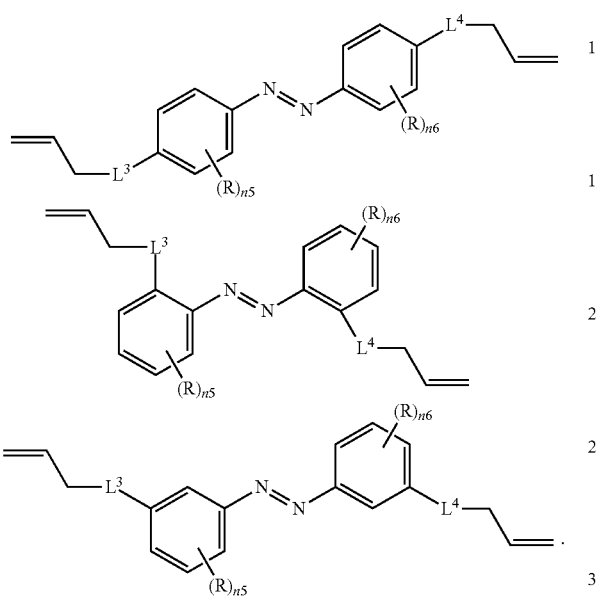

In some embodiments, the masking compound is described by the structure of formula (IV) or (V):

where $R^1$-$R^8$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide. Any convenient counterion may be used for masking compounds described by formula (V). Examples include chloride, iodide, and the like.

In some embodiments, the masking compound is described by the structure of formula (VI):

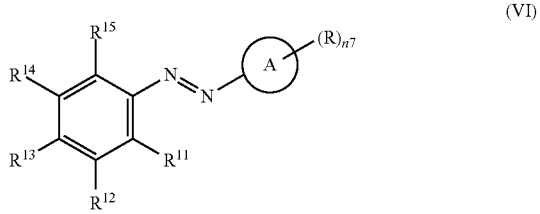

where A is a heterocycle ring;
$n^7$ is 0 or an integer from 1 to 5;
each R is independently selected from the group consisting of hydrogen, $L^5$-$(Z^5)_m$ where m is 1, 2 or 3, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide; and
$R^{11}$-$R^{15}$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide, and $L^5$-$Z^5$;
where $L^5$ is a linker and each $Z^5$ is independently a polymerizable group or a crosslinking group.

In some embodiments, the masking compound is described by the structure of formula (VII):

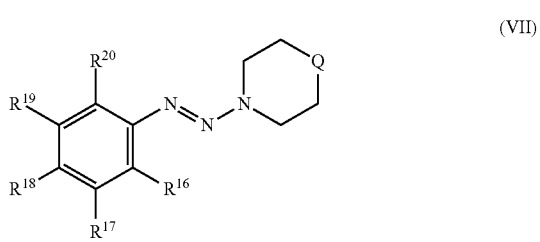

where Q is O or N—$R^{21}$, where $R^{21}$ is hydrogen, an alkyl, an aryl, an acyl, a heterocycle, or —$L^5$-$Z^5$;
$R^{16}$—$R^{20}$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide, and —$L^5$—$Z^5$; and
where each $L^5$ is a linker and each $Z^5$ is a polymerizable group.

In some embodiments, the masking compound is described by one of the following structures:

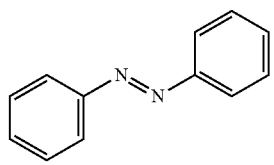

-continued

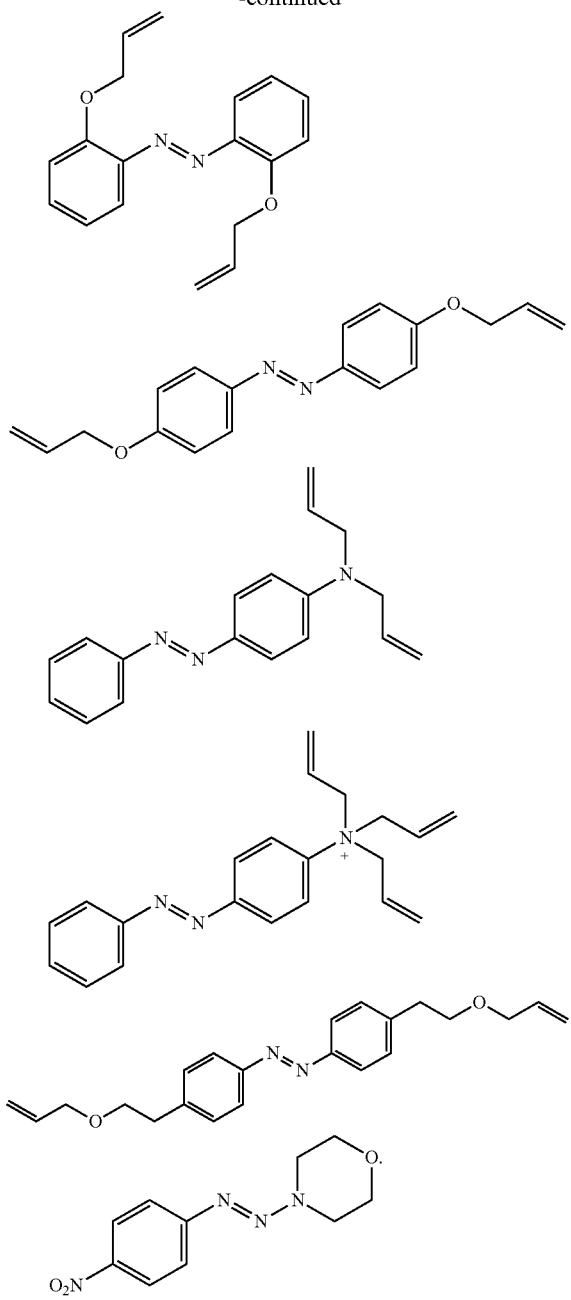

Definitions

Figure 1:
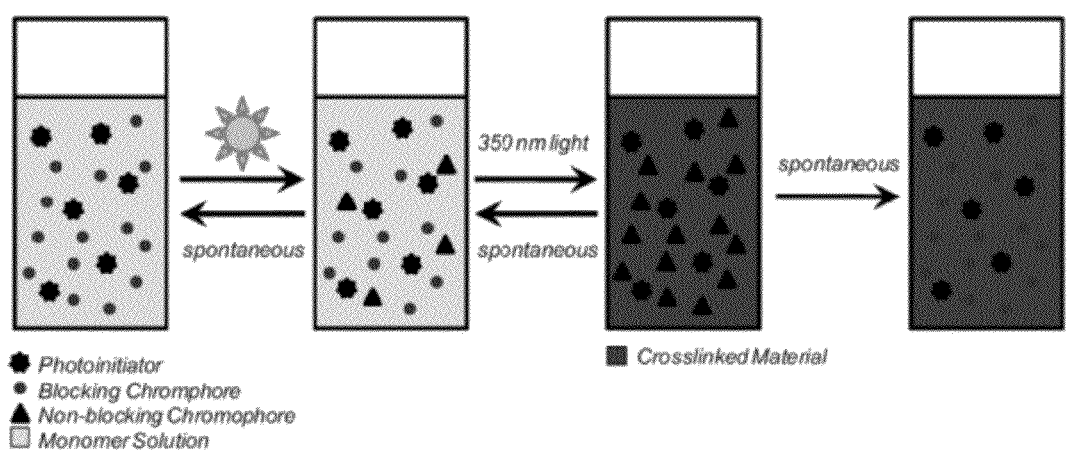
FIG. 1 illustrates a general schematic of an exemplary photopolymerizable prepolymer composition that includes a photoinitiator (star), a masking compound (i.e., blocking chromophore) and a monomer solution, that can resist initiation of polymerization due to sunlight. The first and second panels show the interconversion of some blocking chromophore to non-blocking chromophore (circles and triangles, respectively) in ambient sunlight. The second and third panels shows the complete conversion of masking compound (i.e., blocking chromophore) to a non-blocking form by irradiation with light (e.g., 350 nm). In addition, the third and fourth panels show crosslinking of the unmasked prepolymer solution to a crosslinked material.

Unless otherwise indicated, the disclosure is not limited to specific procedures, materials, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "alkylene" as used herein refers to a di-radical alkyl group. Unless otherwise indicated, such groups include saturated hydrocarbon chains containing from 1 to 24 carbon atoms, which may be substituted or unsubstituted, may contain one or more alicyclic groups, and may be heteroatom-containing. "Lower alkylene" refers to alkylene linkages containing from 1 to 6 carbon atoms. Examples include, methylene (—$CH_2$—), ethylene (—$CH_2CH_2$—), propylene (—$CH_2CH_2CH_2$—), 2-methylpropylene (—$CH_2$—CH($CH_3$)—$CH_2$—), hexylene (—$(CH_2)_6$—) and the like.

Similarly, the terms "alkenylene," "alkynylene," "arylene," "aralkylene," and "alkarylene" as used herein refer to di-radical alkenyl, alkynyl, aryl, aralkyl, and alkaryl groups, respectively.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). The above-mentioned hydrocarbyl moieties may be further substituted with one or more functional groups or additional hydrocarbyl moieties such as those specifically enumerated.

By the term "functional groups" is meant chemical groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$), mono- and di-($C_1$-$C_{24}$ alkyl)-substituted phosphino, mono- and di-($C_5$-$C_{20}$ aryl)-substituted phosphine. In addition, the aforementioned functional groups may, if a particular group permits, be further substituted with one or more additional functional groups or with one or more hydrocarbyl moieties such as those specifically enumerated above.

By "linking" or "linker" as in "linking group," "linker moiety," etc., is meant a multivalent (e.g., trivalent or bivalent) radical moiety. A linker may be branched or linear, saturated or unsaturated, and of 1 to about 20 atoms in length. Examples of such linking groups include alkylene, alkenylene, alkynylene, arylene, alkarylene, aralkylene, amino, oxy, and linking moieties containing functional groups including, without limitation: amido (—NH—CO—), ureylene (—NH—CO—NH—), imide (—CO—NH—CO—), epoxy (—O—), epithio (—S—), epidioxy (—O—O—), carbonyldioxy (—O—CO—O—), alkyldioxy (—O—(CH$_2$)$_n$—O—), epoxyimino (—O—NH—), epimino (—NH—), carbonyl (—CO—), etc.

When the term "substituted" appears prior to a list of possible substituted groups, it is intended that the term apply to every member of that group. For example, the phrase "substituted alkyl and aryl" is to be interpreted as "substituted alkyl and substituted aryl."

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

Definitions of other terms and concepts appear throughout the detailed description below.

Detailed Description

As summarized above, the present disclosure provides methods of modifying a composition, where the composition includes a masking compound and a prepolymer. The subject compositions and methods find use in adjustable intraocular lenses and the manufacturing, use and modification thereof. The invention relates to lenses that can be modified post-fabrication using photoinitiated polymerization methodologies.

The subject lenses provide for on demand polymerization for lens adjustment, following surgical insertion of the lens into the eye of a patient. Lens adjustment may be controlled to account for changes in the physical environment of the eye around the lens that may occur during healing after eye surgery. In some cases, lens adjustment is performed via photoinitiated polymerization or crosslinking after healing has occurred.

To avoid unwanted photoinitiated polymerization or crosslinking induced by ambient sunlight during healing, masking compounds are included that block such photoinitiation by absorbing light. The photoinitiator and masking compound are selected to have overlapping absorption spectra, such that the masking compound is capable of absorbing sufficient ambient sunlight to prevent activation of the photoinitiator. Upon application of suitable triggering conditions, photoisomerization of the masking compound results in a shift in the absorption maximum of the masking compound away from that of the photoinitiator, such that the absorption spectral overlap of the photoisomerized masking compound and the photoinitiator is substantially reduced at a wavelength suitable for activation of the photoionitiator.

Polymerization of the subject compositions may then be triggered via photoinitiation when desired, i.e. after post-surgical healing is completed.

In some embodiments, photoinitiated polymerization may be triggered without the need for a high intensity UV light that could lead to undesirable damaging side effects in a human eye. Potential undesirable damage may occur to the eye when the masking compound and the photoinitiator when a high intensity UV light is needed to surpass the optical density of the masking compound before activating a photoinitiator of polymerization.

In order to further illustrate certain aspects of the present disclosure, the following specific examples are provided. Before certain embodiments are described in greater detail, it is to be understood that this disclosure is not limited to the certain embodiments described, as such may, of course, vary. It is also to be understood that the terminology used herein is for the purpose of describing particular embodiments only, and is not intended to be limiting, since the scope of the disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Compositions

In some embodiments, the compositions of interest contain at least three components: a matrix material, a masking compound, and a prepolymer. In some embodiments, the prepolymer includes a photoinitiator and a polymerizable moiety. In some embodiments, the prepolymer includes a crosslinking moiety (e.g., a photocrosslinker). In some embodiments, the masking compound is linked to a polymerizable moiety or a crosslinking moiety. In some embodiments, the subject compositions find use in an intraocular lens. Any convenient additional ingredients may be included in the subject compositions, such as, structural materials, excipients, fillers, matrix polymers, colorants, anti-reflection compounds, biocompatibility-enhancing agents, anti-bacterial agents, and the like.

Masking Compounds

The compositions of interest include a masking compound (also referred to herein as a "masking agent" or "masking component"). The masking compound is a molecule that has an absorption spectrum that overlaps that of a prepolymer component, such that the masking compound is capable of blocking the absorption of certain wavelengths of light by prepolymer component (e.g., wavelengths at or near the absorption maximum of the prepolymer component, such as a photoinitiator), until the application of a triggering condition to the masking compound. As used herein, the terms "blocking" and "masking" are used interchangeably. The blocked wavelengths of light may be wavelengths that induce polymerization or crosslinking in the prepolymer (e.g., induce the formation of a polymerization-initiating radical). The masking compound is a molecule that upon application of a suitable triggering condition (e.g., irradiation at a particular wavelength of light, a first wavelength) experiences a change in its absorption spectra—for example, a shift in its absorption maximum. As described above, the masking compound may be referred to as "switchable" because its absorption maximum can be shifted upon application of a triggering condition.

In some embodiments, the subject masking compounds display switchable absorption maxima (e.g., upon photoisomerization) such that a photoinitiator (described in more detail below) can be masked from, or exposed to, irradiation on demand.

In some embodiments, the masking compound blocks or prevents polymerization or crosslinking of the prepolymer in ambient sunlight for a period of 12 hours or more, such as 1 day or more, 2 days or more, 3 days or more, 4 days or more, 5 days or more, 6 days or more, 7 days or more, 14 days or more, or even more.

In some embodiments, the masking compound is a photoisomerizable molecule and application of light of a suitable wavelength to the molecule causes isomerization from a first isomer to a second isomer with a concomitant shift in the absorption maximum. In some embodiments, the application of light to a masking compound to cause photoisomerization is referred to as a "triggering condition", as "triggering" or as "switching" the masking compound. As used herein, the terms "photoisomerizable" and "photoisomerization" refer to a structural change that converts a first isomer of a compound to a second isomer, and which is caused by photoexcitation of the molecule. Photoisomerization may be reversible or irreversible. In some embodiments, thermal relaxation returns the compound to its original state, such that the photoisomerization process can be repeated, e.g., several times.

In some embodiments, the photoisomerizable masking compound has two isomeric forms (i.e., a first isomer and a second isomer) that have significantly different absorption spectra. By significantly different absorption spectra is meant that the difference in absorption maxima between the first and second isomers is about 10 nm or more, 20 nm or more, 30 nm or more, 40 nm or more, 50 nm or more, 60 nm or more, 70 nm or more, 80 nm or more, 90 nm or more, 100 nm or more, 125 nm or more, 150 nm or more, 175 nm or more, or even about 200 nm or more. In some embodiments, the first isomer has an absorption maximum that does not overlap the absorption spectrum (i.e., the region of significant absorption in the IR, visible, and UV wavelengths) of the second isomer. In some embodiments, the second isomer has an absorption maximum that does not overlap the absorption spectrum of the first isomer. In some embodiments, the absorption maximum of the second isomer is at a wavelength where there is substantially less (e.g., 20% less, or 30% less, or 40% less, or 50% less, or 60% less, or 70% less, or 75% less, or greater than 75% less) absorption by the first isomer.

In some embodiments, photoisomerization converts the masking compound from a first isomer to a second isomer, where the second isomer absorbs less light compared with the first isomer at a wavelength that activates a prepolymer component of the subject composition.

In some embodiments, in qualitative terms, the absorption of the first isomer of the masking compound at the wavelength that causes the photoinitiator or photocrosslinker to initiate polymerization or crosslinking is sufficiently large that the presence of the first isomer in solution prevents photoinitiation or photo-induced crosslinking. In contrast, the second isomer absorbs substantially less at that wavelength, and photoinitiation or photocrosslinking becomes possible when a sufficient quantity of the first isomer is converted to the second isomer. A sufficient quantity of such isomer conversion will depend upon the characteristics of the solution (e.g. concentrations of the various components) but will be apparent by the onset of polymerization or crosslinking of the prepolymer (see below for more details).

In some embodiments, the masking compound is isomerized from the first to the second isomer solely by the application of electromagnetic radiation—no thermal energy is required to cause the isomerization.

In some embodiments, as described in more detail herein, after photoisomerization, the masking compound re-isomerizes back to the first isomer over a period of time. The re-isomerization may occur via thermal relaxation (i.e., the rate is a function of the reaction temperature) and/or may be accelerated by application of a stimulus (e.g. electromagnetic radiation). After re-isomerizing back to the first isomer, the masking compound can be isomerized again from the first isomer to the second isomer.

It will be appreciated that the photoisomerization is a reaction, and as such has an associated reaction rate. Such reaction rate can, in some embodiments, be accelerated by application of additional stimulus (e.g., a more intense electromagnetic radiation source, or a plurality of such sources). Application of light at the second wavelength to initiate reaction of the prepolymer (see discussion below) can, in some embodiments, be carried out after complete isomerization of the masking compound (i.e., substantially 100% reaction). In other embodiments, application of light at the second wavelength can be carried out at less than 100% isomerization of the masking compound—e.g., where the concentration of masking compound present as the first isomer has fallen below the level needed to inhibit initiation of reaction of the prepolymer.

In some embodiments, photoisomerization is performed in a photoreactor. In some embodiments, photoisomerization is performed using a monochromatic light source.

In some embodiments, photoisomerization of the masking compound occurs via a cis-trans isomerization, a cyclization reaction, or a ring-opening reaction. Convenient photoisomerizable compounds that may be used as the subject masking compounds include compounds that are capable of blocking absorption of a suitable prepolymer component (e.g., a photoinitiator) and that experience a significant shift in absorption maxima upon application of a suitable triggering condition. In some embodiments, the masking compound undergoes a cyclization or ring-opening photoisomerization upon absorption of electromagnetic energy at the first wavelength (e.g., a triggering condition). In some embodiments, the masking compound includes a photoisomerizable moiety that is a stilbene (e.g., an azastilbene), an azobenzene moiety, an azoarylene, a fulgide, a spiropyran, a naphthopyran, a quinone, a spiro-oxazine, a nitrone, a triaryl methane (e.g., a triphenyl methane), a thioindigo, a diarylethene, a dithienylethene, or an overcrowded alkene. In some embodiments, the masking compound includes an alkenyl (C=C) or an azo moiety (—N=N—) moiety that undergoes photoisomerization via a cis-trans transition. In some embodiments, the masking compound includes a diarylethene that undergoes photoisomerization via an electrocyclic cyclization reaction. In some embodiments, the masking compound includes a spiropyran that undergoes photoisomerization via a ring opening transition.

In some embodiments, the photoisomerizable moiety is selected from an azoarylene, a diarylethene, and a dithienylethene.

In some embodiments, photoisomerization of the masking compound results in a second isomer that is thermally unstable, e.g., the second isomer will revert to the first isomer when the light source is removed. In such cases, photoisomerization is reversible.

In some embodiments, the masking compound includes a photoisomerizable moiety linked to one or more polymerizable moieties. In some embodiments, the masking compound is described by the formula:

$$(Z^1)_{n1}—Y—(Z^2)_{n2} \quad (I)$$

where Y is a photoisomerizable moiety (e.g., as described above);

$n^1$ and $n^2$ are each independently 0, 1, 2 or 3; and each $Z^1$ and $Z^2$ is independently a polymerizable moiety or a crosslinking moiety that is connected to Y via an optional linker.

In some embodiments, in formula (I), $n^1$ and $n^2$ are each 1, and $Z^1$ and $Z^2$ are each independently connected to Y via a linker of 1 to 20 atoms in length (e.g., 1 to 6 atoms in length). In some embodiments, in formula (I), Y is an azoarylene, a diarylethene, or a dithienylethene. In some embodiments, in formula (I), each $Z^1$ and $Z^2$ is independently selected from a vinyl, a vinylidene, a diene, an olefin, an allyl, an acrylate, an acrylamide and an acrylic acid.

In some embodiments, the masking compound has the structure $Ar^1-N=N—Ar^2$ or $Ar^1-C=C—Ar^2$, where $Ar^1$ and $Ar^2$ are independently selected from aromatic 6-membered rings that may be substituted or unsubstituted and may include one or more heteroatoms. In some embodiments, the masking compound includes an azobenzene moiety (e.g., where $Ar^1$ and $Ar^2$ are phenyl). In some embodiments, the masking compound is capable of photoisomerization from a trans isomer to a cis isomer, e.g., as exemplified for the $Ar^1—N=N—Ar^2$ compound below shown below. In some embodiments, the cis isomer of the masking compound spontaneously isomerizes back to the trans isomer.

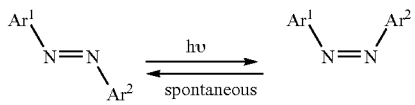

In some embodiments, the azobenzene moiety is a photoisomerizable chromophore having absorption maximum near that of a photoinitiator (such as any of the photoinitiators used and described herein). In some embodiments, the azobenzene moiety has an absorption maximum about 50 nm or less (e.g., about 40 nm or less, about 30 nm or less, about 20 nm or less, or about 10 nm or less) from the absorption maximum of the photoinitiator. In some embodiments, the thermodynamically more stable trans-azobenzene (t-AB) moiety tends to absorb at lower wavelengths than the corresponding cis-azobenzene (c-AB) isomer. Upon irradiation, photoisomerization may be facile and quantitative. In some embodiments, thermal relaxation from the c-AB moiety to the t-AB isomer occurs within hours (e.g., within 12 hours or less, such as 6, 5, 4, 3, 2 or within 1 hour or less) at ambient temperature. Irradiation of the t-AB moiety near its absorption maximum causes isomerization to the cis isomer and a change in the absorption spectrum (e.g., a shift in the absorption maxima).

In some embodiments, the masking compound further includes a polymerizable moiety, i.e., a functional group capable of polymerization in a prepolymer composition upon application of a suitable stimulus (e.g., activation of a photoinitiator). The polymerizable moiety may include a functional group such as an alkenyl, a vinyl, a vinylidene, a diene, an olefin, an allyl, an acrylate or a (meth)acrylic functional group. In some embodiments, the polymerizable moiety is an allyl or a vinyl group.

In some embodiments, where the masking compound comprises a polymerizable moiety, the masking compound may be chemically incorporated into another component of the compositions of interest. For example, the masking compound can be incorporated into the backbone of a polymer that is present as a matrix material (see below). Also for example, the masking compound can be incorporated into the backbone or as a sidegroup of the prepolymer (see below). In this way, small molecule masking compounds can be chemically incorporated into polymeric components of the compositions of interest. In some embodiments and for some applications, incorporating masking compounds in this manner makes it less likely for the masking component to diffuse out of the compositions of interest.

In some embodiments, the masking compound is described by the structure of formula (II):

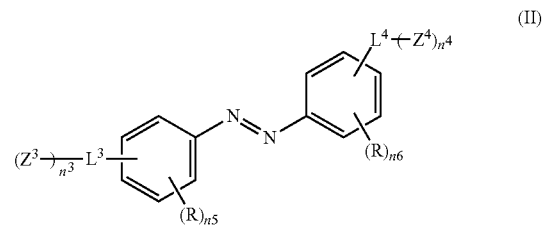

where:

$n^3$ and $n^4$ are each independently 0, 1, 2 or 3;

each $Z^3$ and $Z^4$ is independently a polymerizable moiety or a crosslinking moiety;

$L^3$ and $L^4$ are linkers;

$n^5$ and $n^6$ are each independently 0, 1, 2, 3, 4 or 5, provided that when $(Z^3)_{n3}$-$L^3$- is present, $n^5$ is not 5, and when -$L^4$-$(Z^4)_{n4}$ is present, $n^6$ is not 5; and each R is independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide.

In some embodiments, in formula (II), each $Z^3$ and $Z^4$ is independently selected from a vinyl, a vinylidene, a diene, an olefin, an allyl, an acrylate, an acrylamide and an acrylic acid.

In some embodiments, in formula (II), $L^3$ and $L^4$ are each independently a linker of 1 to 20 atoms in length, such as of 1 to 6 atoms in length. In some embodiments, in formula (II), the linker $L^3$ and/or $L^4$, when present, may include an amino group that connects to a polymerizable moiety or a crosslinking moiety. In some embodiments, a linker is present and includes a branched amino group (e.g., a trivalent amino or a tetravalent ammonium group) for connecting two or three polymerizable moieties and/or crosslinking moieties to the azobenzene. In some embodiments, in formula (II), $L^3$ and/or $L^4$ is a branched amino (—N═) group. In some embodiments, in formula (II), $L^3$ and/or $L^4$ is a branched ammonium (—N(+)═) group. In some embodiments, in formula (II), $L^3$ includes a branched amino or ammonium group, $n^3$ is 2 or 3, and $Z^3$ is an allyl or a vinyl.

In some embodiments, in formula (II), $L^3$ and $L^4$, when present, may be attached to the azobenzene ring at any convenient positions. For example, $L^3$ may be attached to the first phenyl ring at the 2, 3 or 4 position relative to the azo substituent. For example, $L^4$ may be attached to the second phenyl ring at the 2', 3' or 4' position relative to the azo substituent. All combinations of $L^3$ and/or $L^4$ positioning around the first and second phenyl rings, respectively, are envisaged. For example, $L^3$ and $L^4$ may be attached at the 2 and 2' positions, respectively. For example, $L^3$ and $L^4$ may be attached at the 3 and 3' positions, respectively. For example, $L^3$ and $L^4$ may be attached at the 4 and 4' positions (i.e., para), respectively. Alternatively, $L^3$ may be attached at the 4-position of the first phenyl ring, and $L^4$ may be attached at the 2' position of the second phenyl ring. Exemplary arrangements of $L^3$ and $L^4$ are shown in the compounds described below.

In some embodiments, the masking compound is described by the structure of Formula (III):

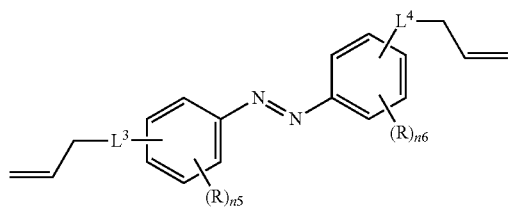

(III)

where $L^3$ and $L^4$ are linkers;

$n^5$ and $n^6$ are each independently 0, 1, 2, 3 or 4; and each R is independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide.

In some embodiments, the masking compound is as described by the structure of Formula (III) except that one or both of the terminal allyl groups may be independently replaced with any convenient polymerizable moiety or crosslinking moiety, as described herein.

In some embodiments, in Formula (III), one or both of $L^3$ and $L^4$ are connected to the azobenzene via an electron withdrawing substituent, such as, a carbonyl, an ester, an amido, a sulfonyl or a sulfonamide. In some embodiments, in Formula (III), $L^3$ and $L^4$ are independently —(CH$_2$)$_{m1}$—Z$^4$—(CH$_2$)$_{m2}$— where $m^1$ and $m^2$ are each independently 0 or an integer from 1 to 6, and $Z^4$ is selected from a carbonyl (—C(═O)—), an ester (—C(═O)O—), an amido (e.g., —C(═O)NH—), a carbamate (e.g., —OC(═O)NH—), a sulfonyl (—SO$_2$—), a sulfonamide (e.g., —SO$_2$NH—), an ether (—O—), a thioether (—S—) or a urea group (e.g., —NHC(═NH)NH—). In some embodiments, $m^1$ is 2 and $m^2$ is 0. In some embodiments, $Z^4$ is —O—.

In some embodiments, the masking compound is described by one of the following structures:

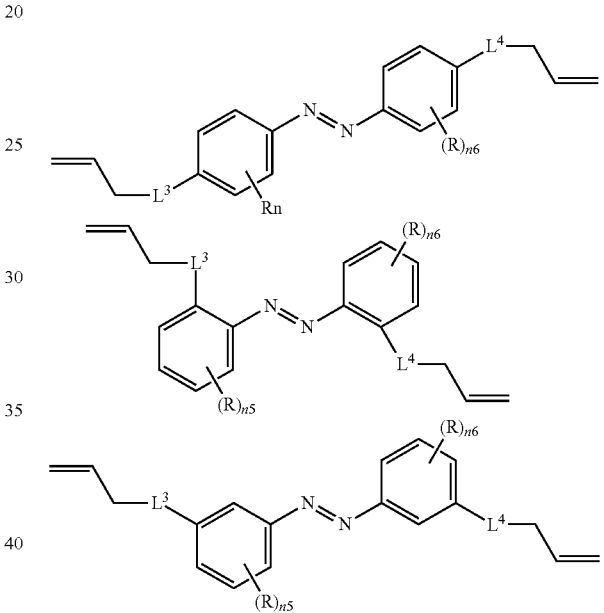

where $L^3$, $L^4$, $(R)_{n5}$ and $(R)_{n6}$ are defined above for Formula (III). In certain embodiments, $L^3$ and $L^4$ are independently selected from —O— and —O(CH$_2$)$_m$— where m is an integer from 1 to 6, (e.g., m is 2). In some embodiments, each R is hydrogen.

In some embodiments, the masking compound is described by the structure of Formula (IV) or (V):

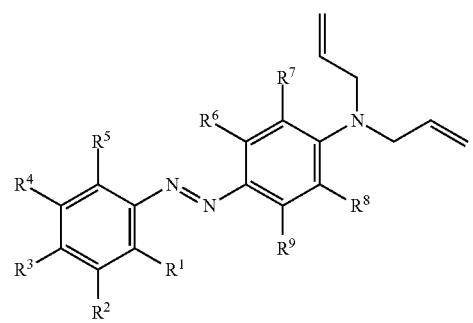

(IV)

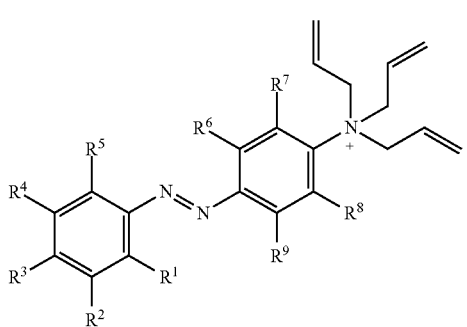

(V)

where $R^1$-$R^8$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide.

In some embodiments, in Formula (IV) or (V), one or more of $R^1$-$R^8$ is -$L^5$-O—$CH_2CH=CH_2$, where $L^5$ is an optional linker group. In some embodiments, in Formula (IV) or (V), each $L^5$ is a $C_1$-$C_6$ alkyl chain (e.g., a $C_2$ alkyl). In some embodiments, in Formula (IV) or (V), each $L^5$ is absent. In some embodiments, in Formula (IV) or (V), $R^1$-$R^8$ are each hydrogen.

In some embodiments, the masking compound is described by the structure of Formula (VI):

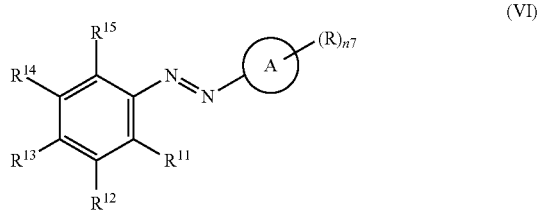

(VI)

where A is a heterocycle ring;

$n^7$ is 0 or an integer from 1 to 5;

each R is independently selected from the group consisting of hydrogen, -$L^5$-$(Z^5)_m$ where m is 1, 2 or 3, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide; and $R^{11}$-$R^{15}$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamidea hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide, and -$L^5$-$Z^5$;

where $L^5$ is a linker and each $Z^5$ is independently a polymerizable group or a crosslinking group.

In some embodiments, in formula (VI), A is a N-linked heterocycle, such as but not limited to, morpholino, thiomorpholino piperidino, piperazino, homopiperazine, azepano, or pyrrolidino.

In some embodiments, in formula (VI), A is a N-linked heterocycle (e.g., an N-morpholino or a N-piperidinyl). In some embodiments, the masking compound is described by the structure of formula (VII):

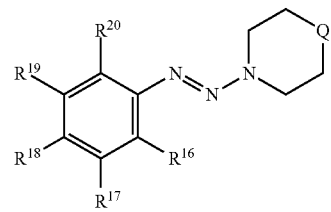

(VII)

where Q is O or N—$R^{21}$, where $R^{21}$ is hydrogen, an alkyl, an aryl, an acyl, a heterocycle, or -$L^5$-$Z^5$;

$R^{16}$-$R^{20}$ are each independently selected from the group consisting of hydrogen, a hydrocarbyl (e.g., alkyl, alkenyl, aryl, etc.), a heterocycle, a halogen, a haloalkyl or perhaloalkyl (e.g., trifluoromethyl), an amino, hydroxyl, an ether, nitro, cyano, carboxy, an acyl, an amido, an ester, a thiol, a thioether, a sulfonyl and a sulfonamide, and -$L^5$-$Z^5$; and where each $L^5$ is a linker and each $Z^5$ is a polymerizable group or a crosslinking group.

In some embodiments, in Formula (VII), each $L^5$ is independently a $C_1$-$C_6$ alkyl chain (e.g., a $C_2$ alkyl).

In some embodiments, in Formula (VII), at least one (e.g., two) of $R^{16}$-$R^{20}$ and $R^{21}$ includes a polymerizable moiety (e.g., an allyl group) or a crosslinking moiety. In some embodiments, in Formula (VII), at least one of $R^{16}$-$R^{20}$ and $R^{21}$ includes an allyl or a vinyl group. In some embodiments, in Formula (VII), $R^{18}$ is —$(CH_2)_{m1}$-$L^6$-$(CH_2)_{m2}$—$Z^5$ where $m^1$ and $m^2$ are each independently 0 or an integer from 1 to 6, and $L^6$ is selected from a carbonyl (—C(=O)—), an ester (—C(=O)O—), an amido (e.g., —C(=O)NH—), a carbamate (e.g., —OC(=O)NH—), a sulfonyl (—$SO_2$—), a sulfonamide (e.g., —$SO_2$NH—), an ether (—O—), a thioether (—S—) or a urea group (e.g., —NHC(=NH)NH—). In some embodiments, $m^1$ is 2 and $m^2$ is 0. In some embodiments, $L^6$ is —O—.

In some embodiments, at least one of $R^{16}$-$R^{20}$ and $R^{21}$ (e.g., $R^{18}$, $R^{19}$ or $R^{20}$) is -$L^7$-O—$CH_2CH=CH_2$, where $L^7$ is an optional linker group. In some embodiments, in Formula (VII), each $L^7$ is independently a $C_1$-$C_6$ alkyl chain (e.g., a $C_2$ alkyl).

In some embodiments, in Formula (VII), Q is O. In some embodiments, in Formula (VII), one or more of $R^{16}$-$R^{20}$ is nitro. In some embodiments, in Formula (V), $R^{18}$ is nitro, and $R^{16}$, $R^{17}$, $R^{19}$ and $R^{20}$ are hydrogen.

In some embodiments, the masking compound is selected from one of the following structures:

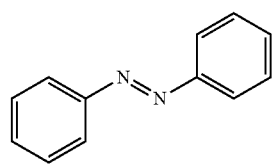

azobenzene

-continued

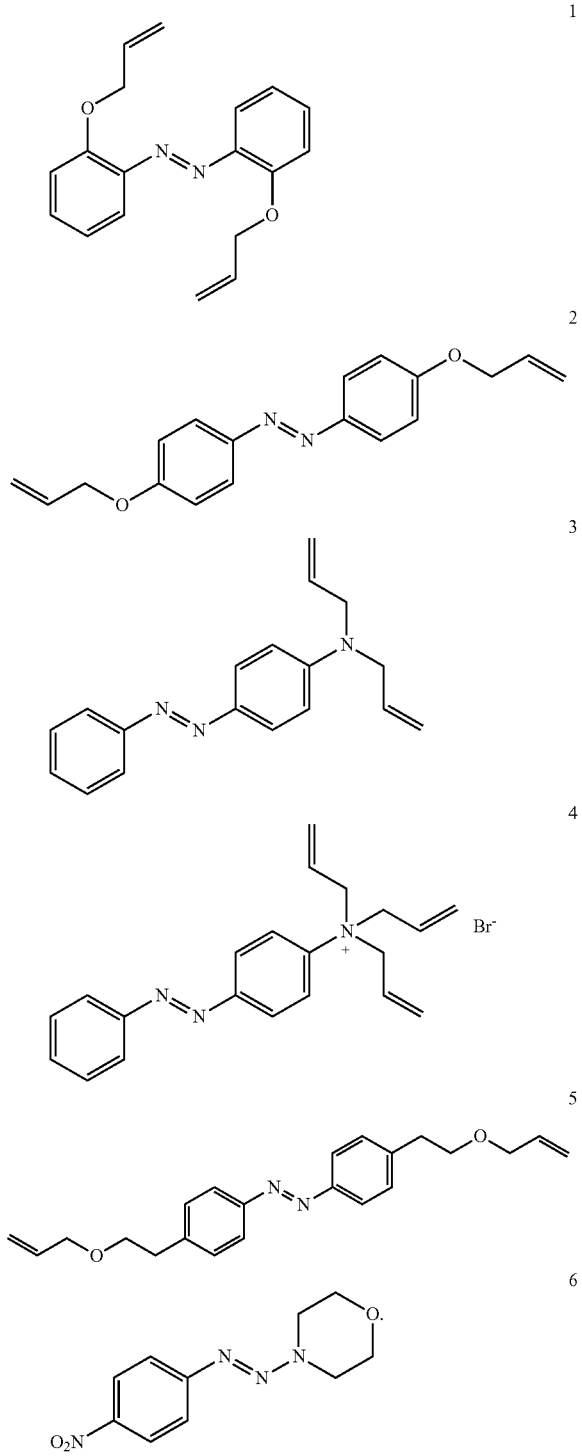

Prepolymer

The compositions of interest may include a prepolymer. The prepolymer is a material capable of undergoing a reaction (e.g., polymerization, crosslinking, etc.), and capable of modifying one or more properties of the composition via such reaction. In some embodiments, the prepolymer is a single component, whereas in other embodiments, the prepolymer is a composition comprising two or more components. At least one of the components in the prepolymer (or the sole component, where the prepolymer consists of only one component) is a material that can undergo a reaction such as a polymerization or crosslinking reaction. Such component may be a small molecule such as a monomer or oligomer, or may be a polymer.

In some embodiments where the prepolymer is a single component, the prepolymer is capable of absorbing light that self-initiates the modification reaction (e.g., polymerization, crosslinking, etc.) in the single component. In some embodiments where the prepolymer is a multi-component composition, the prepolymer includes a prepolymer component that is capable of absorbing light to induce the modifying reaction (e.g., polymerization, crosslinking, etc.) in the prepolymer. In some such embodiments, the prepolymer component is a photoinitiator. In some such embodiments, the prepolymer component is crosslinking moiety.

In some embodiments, the prepolymer includes a photoinitiator and a polymerizable moiety and the modifying reaction is a polymerization reaction. In some embodiments, the polymerization reaction is a radical polymerization. In some embodiments, the prepolymer includes a crosslinking moiety (e.g., a photocrosslinker) and a crosslinkable monomer or oligomer and the modifying reaction is a crosslinking reaction.

In some embodiments, the shifted absorption maximum of the masking compound (i.e., the maximum of the second isomer) no longer significantly overlaps the absorption spectrum of a photoinitiator present in the subject composition. Because of the reduced absorbance of the masking compound, polymerization of the prepolymer of the subject composition becomes possible upon irradiation with light of a suitable wavelength and intensity. Such application of light to cause polymerization is referred to herein as a polymerization or crosslinking condition or a polymerization or crosslinking step.

In some embodiments, the electromagnetic energy of the polymerization condition induces polymerization of the prepolymer indirectly via activation of a photoinitiator (e.g., by the absorption of light of a suitable wavelength and intensity). In some embodiments, the electromagnetic energy of the polymerization condition induces polymerization (e.g., by the absorption of light of a suitable wavelength and intensity) by direct initiation of the prepolymer. By direct initiation is meant that the polymerization condition induces polymerization of a polymerizable moiety directly rather than via contact with a photoinitiator.

In some embodiments, polymerization is not induced thermally, e.g., by activation of a thermal initiator.

In some embodiments, suitable polymerization conditions include wavelengths of light of between about 1 and about 800 nm, such as, between about 200 and about 800 nm, between about 300 and about 650 nm, between about 300 and about 500 nm, between about 300 and about 400 nm, between about 340 and about 370 nm (e.g., about 365 nm), or between about 340 and about 350 nm. In some embodiments, the triggering and polymerization conditions are the same. In some embodiments, in the subject methods, the triggering and polymerization steps are performed concurrently, e.g., substantially at the same time. In some embodiments, the triggering and polymerization conditions include applying electromagnetic energy from the same light source. In some embodiments, the triggering and polymerization conditions include applying electromagnetic energy from different light sources. In some embodiments, the electromagnetic energy of the light is optionally generated from a monochromatic source, such as a laser. In other embodiments, the light is generated by a polychromatic source (e.g., ambient sunlight).

In some embodiments, the photoinitiator is a benzoin-type photoinitiator (e.g., 2,2-dimethoxy-1,2-diphenylethan-1-one). In some embodiments, the photoinitiator is an aryl peroxide (e.g., benzoyl peroxide).

Exemplary photoinitiators include but are not limited to, 2,2-dimethoxy-1,2-diphenylethan-1-one, benzoyl peroxide, benzoin, benzyl, hydroxyacetophenone, dimethylbenzil, di-tert-butyl peroxide, AIBN and analogues thereof, etc.

In some embodiments, the polymerizable moiety includes one or more olefinic double bonds. They may be of low (monomeric) or high (oligomeric) molecular mass. In some embodiments, the polymerizable moiety includes a vinyl, a vinylidene, a diene, an olefin, an allyl, an acrylate, an acrylamide or an acrylic acid. In some embodiments, the prepolymer includes a polymerizable monomer—i.e. a monomer containing at least one polymerizable moiety.

Examples of polymerizable monomers containing a double bond include alkyl, aryl, hydroxyalkyl, cycloalkyl (optionally including an O) or amino acrylates, or alkyl, hydroxyalkyl, cycloalkyl (optionally including an O) or amino methacrylates, for example methyl, ethyl, butyl, 2-ethylhexyl, phenyl or 2-hydroxyethyl acrylate, tetrahydrofurfuryl acrylate, isobornyl acrylate, methyl methacrylate, cyclohexyl methacrylate or ethyl methacrylate, hydroxyalkyl acrylates such as 2-hydroxyethyl acrylate, etheralkyl acrylates such as 2-methoxyethyl acrylate, alkoxy- or aryloxy-poly(alkylene glycol) acrylates such as methoxypoly(ethylene glycol)acrylates, ethoxypoly(ethylene glycol)acrylates, polyethylene glycol diacrylate, methoxypoly(propylene glycol)acrylates, methoxypoly(ethylene glycol)-poly(propylene glycol)acrylates or their mixtures, aminoalkyl acrylates such as 2-(dimethylamino)ethyl acrylate (DMAEA), fluoro acrylates, silyl acrylates, phosphorus acrylates such as alkylene glycol phosphate acrylates, methacrylic monomers such as methacrylic acid or its salts, alkyl, cycloalkyl, alkenyl or aryl methacrylates, such as methyl methacrylate (MMA), lauryl methacrylate, cyclohexyl methacrylate, allyl methacrylate, phenyl methacrylate or naphthyl methacrylate, hydroxyalkyl methacrylates such as 2-hydroxyethyl methacrylate or 2-hydroxypropyl methacrylate, etheralkyl methacrylates such as 2-ethoxyethyl methacrylate, alkoxy- or aryloxy-poly(alkylene glycol) methacrylates such as methoxypoly(ethylene glycol)methacrylates, ethoxypoly(ethylene glycol)methacrylates, methoxypoly(propylene glycol)methacrylates, methoxypoly(ethylene glycol)-poly(propylene glycol)methacrylates or their mixtures, aminoalkyl methacrylates such as 2-(dimethylamino)ethyl methacrylate (DMAEMA), fluoro methacrylates such as 2,2,2-trifluoroethyl methacrylate, silyl methacrylates such as 3-methacryloylpropyltrimethylsilane, and phosphorus methacrylates such as alkylene glycol phosphate methacrylates, hydroxyethylimidazolidone methacrylate, hydroxyethylimidazolidinone methacrylate, or 2-(2-oxo-1-imidazolidinyl)ethyl methacrylate.

Silicone acrylates may also be used. Further exemplary polymerizable moieties include acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride. Further exemplary polymerizable moieties include: vinylaromatic monomers such as styrene or substituted styrenes, (e.g., alpha-methylstyrene), acrylonitrile, acrylamide or substituted acrylamides, 4-acryloylmorpholine, N-methylolacrylamide, methacrylamide or substituted methacrylamides, trimethylolpropane triacrylate (TPT), acryloyl chloride, N-methylolmethacrylamide, methacrylamidopropyltrimethyl ammonium chloride (MAPTAC), itaconic acid, maleic acid or its salts, maleic anhydride, alkyl or alkoxy- or aryloxy-poly (alkylene glycol) maleates or hemimaleates, vinyl alcohols, vinylpyridine, vinylpyrrolidinone, (alkoxy) poly(alkylene glycol)vinyl ether or divinyl ether, such as methoxy poly(ethylene glycol)vinyl ether, poly(ethylene glycol)divinyl ether, olefin monomers, among which mention may be made of ethylene, butene, hexene and 1-octene and also fluoro olefin monomers, and vinylidene monomers, among which mention may be made of vinylidene fluoride, these monomers being used alone or as a mixture of at least two aforesaid monomers.

Examples of polymerizable monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (polymerizable oligomers) are acrylated epoxy resins, polyesters containing acrylate-, vinyl ether- or epoxy-groups, and also polyurethanes and polyethers. Further examples of unsaturated polymerizable oligomers are unsaturated polyester resins, which are usually prepared from maleic acid, phthalic acid and one or more diols and have molecular weights of from about 500 to 3000. In addition, vinyl ether monomers and oligomers may be used, and also maleate-terminated oligomers with polyester, polyurethane, polyether, polyvinyl ether and epoxy main chains. In some embodiments, copolymers of vinyl ether and maleic acid-functionalized monomers are also suitable.

Examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

In some embodiments, the polyols are aromatic, aliphatic or cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the abovementioned polyols, e.g., the aromatic polyols, and epichlorohydrin. Other suitable polyols are polymers and copolymers containing hydroxyl groups in the polymer chain or in side groups, examples being polyvinyl alcohol and copolymers thereo, or polyhydroxyalkyl methacrylates or copolymers thereof. Further polyols which are suitable are oligoesters having hydroxyl end groups.

Examples of aliphatic and cycloaliphatic polyols are alkylenediols having e.g., 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(beta-hydroxyethyl) amine, trimethylolethane, trimethylolpropane, pentaerythritol, dipentaerythritol and sorbitol. The polyols may be partially or completely esterified with one carboxylic acid or with different unsaturated carboxylic acids, and in partial esters the free hydroxyl groups may be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as polymerizable moieties are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-beta-aminoethyl ether, diethylenetriamine, triethylenetetramine, di(beta-aminoethoxy)- or di(beta-aminopropoxy)ethane. Other suitable polyamines are polymers and copolymers, e.g., with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, beta-methacrylamidoethyl methacrylate and N-[(beta-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, e.g., from those with relatively long chains of, for example 6 to 20 C atoms. Examples of polyurethanes are those composed of saturated or unsaturated diisocyanates and of unsaturated or, respectively, saturated diols.

Polymers with (meth)acrylate groups in the side chain may also be used. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

Other suitable polymers with acrylate or methacrylate groups in the side chains are, for example, solvent soluble or alkaline soluble polyimide precursors, for example poly (amic acid ester) compounds, having the photopolymerizable side groups either attached to the backbone or to the ester groups in the molecule.

In some embodiments, the methods of interest convert the prepolymer to a modified polymer. In some embodiments, the modified polymer is a crosslinked composition. In other embodiments, the modified polymer is not crosslinked but has a molecular weight higher than the prepolymer. The methods of interest may convert the prepolymer to the modified polymer in a single polymerization reaction, or the conversion may occur over the course of several polymerization reactions.

In some embodiments, the prepolymer includes a crosslinkable monomer or oligomer and an optional crosslinking moiety (e.g., a photocrosslinker). In some embodiments, the crosslinkable monomer or oligomer is selected from acrylates, methacrylates, vinyl alcohols, polyacrylates, polymethacrylates, vinyl polymers, polyalkylene oxides, polysiloxanes, polyvinylpyrroles, polyamino acids, polysaccharides, and polynucleic acids, as well as copolymers thereof. Such crosslinkable monomers and oligomers may be substituted or unsubstituted. Some specific exemplary crosslinkable monomer or oligomers include polymethyl methacrylate (PMMA), polyvinyl alcohol (PVA), polydimethyl siloxane.

Matrix Material

The compositions of interest contain a matrix material. In some embodiments, the matrix material is a composition containing one or more components and performing one or more functions. For example, components of the matrix material include one or more of matrix polymers, colorants, anti-reflection compounds, biocompatibility-enhancing agents, anti-bacterial agents, and the like.

The matrix material serves one or more functional roles. In some embodiments, for example, the matrix material serves as a structural material, and may be either flexible or rigid. In some embodiments, prior to polymerization of the prepolymer (discussed herein), the matrix material imparts structural form and stability to the compositions of interest. The matrix material may also serve as a carrier for other components (e.g. the masking component, prepolymer, additives, etc.).

In some embodiments, the matrix material is a polymer. Example classes of suitable polymer matrix materials include polyacrylates, polymethacrylates, vinyl polymers, polyalkylene oxides, polysiloxanes, polyvinylpyrroles, polyamino acids, polysaccharides, and polynucleic acids, as well as copolymers thereof. Such polymers may be substituted or unsubstituted. Some specific example matrix polymers include polymethyl methacrylate (PMMA), polyvinyl alcohol (PVA), and polydimethyl siloxane.

Many colorants, anti-reflection compounds, biocompatibility-enhancing agents, anti-bacterial agents, etc. are known and are suitable to be included in the matrix material, and may be incorporated according to the desired application.

In some embodiments, the matrix material comprises a polymeric material, and the masking compound is chemically incorporated (e.g., via polymerization through a vinyl group attached to the masking compound) into the polymeric material.

Lenses

Aspects of the disclosure include adjustable lenses. Any of the subject compositions described above may be used in preparing the subject lenses. By adjustable is meant that one or more properties of the lens (e.g., an optical property such as refractive index, or a physical property such as thickness, rigidity, or the like) may be changed or modified in a controlled fashion, e.g., by practicing the subject methods described herein. In some embodiments, the subject lenses are modified in a location specific manner by controlling the exposure of different portions of the lens to electromagnetic energy (e.g., via masking or light directing optics).

In some embodiments, the subject adjustable lens is an intraocular implant. In some embodiments, the subject lens includes a masking compound and a prepolymer. The masking compound is capable of photoisomerization between a first isomer and a second isomer upon absorption of electromagnetic energy at a first wavelength and intensity (e.g., a triggering condition). The prepolymer is capable of polymerization or crosslinking upon photoinitiation with electromagnetic energy at a second wavelength and intensity (e.g., a polymerization or crosslinking condition).

In some embodiments, one or more properties (e.g., optical power, refractive index, volume, thickness, etc.) of the subject lenses may be adjusted (e.g., increased or decreased) using the subject methods described herein. In some embodiments, polymerization or crosslinking of the prepolymer in a lens composition can be performed to produce a change in the volume of the lens. For example, the portion of the subject lens that is exposed to a photoinitiating electromagnetic energy to induce polymerization or crosslinking may change the volume of the exposed lens composition. In some embodiments, polymerization or crosslinking in the exposed portion of the lens leads to an increase in volume or a change in composition that causes a decrease in the refractive index. In some embodiments, polymerization or crosslinking in the exposed portion of the lens leads to a decrease in volume or a change in composition that causes an increase in the refractive index. The effects of crosslinking and polymerization on the optical properties of the subject lenses may be determined using any convenient methods, such as the Lorentz-Lorenz equation, which expresses the refractive index in terms of a molar refractivity and molar volume.

In some embodiments, the subject lens composition does not contain free polymerizable monomer, and upon exposure to ultraviolet radiation, crosslinking occurs between polymers in the exposed portion of the lens.

In some embodiments, polymerization or crosslinking of the prepolymer in a lens composition can be performed to produce a refractive index change in the lens that was controllable, reproducible, and adjustable.

As described herein, the masking compound is capable of blocking polymerization or crosslinking of the prepolymer, until photoisomerization of the compound is triggered, and the masking compound is converted from a first isomer to a second isomer having a different absorption profile. In some embodiments, the first isomer of the masking compound absorbs more light at the second wavelength than the second isomer of the masking compound. In such cases, the first isomer of the masking compound can block polymerization of the prepolymer by absorbing ambient sunlight at wavelengths that induce polymerization or crosslinking (e.g., the second wavelength). The absorption maximum of the second isomer of the masking compound may be sufficiently shifted from that of the first isomer such that the prepolymer is no longer masked (e.g., prevented from undergoing a photoinitiated modifying reaction).

In some embodiments, the subject lens further includes a matrix material. Any convenient matrix material may be used to provide structure to the subject lenses. In general, the matrix materials of the subject lenses may fall into the following categories: hydrogels; silicones; and non-hydrogel acrylics. In some embodiments, the matrix material of the subject lens is a polymer selected from a polyacrylate, a polymethacrylate and a polysiloxane. In some embodiments, the subject lens includes soft, foldable materials, which are easier to insert into the eye through a small incision in the eye.

Methods

Aspects of the disclosure include methods of implanting and modifying the subject compositions and lenses.

In some embodiments, the method is a method for implanting and modifying an intraocular implant, such as a lens. In some embodiments, the subject method includes inserting the intraocular implant into the eye of a patient, allowing the eye to heal for a period of time, applying a triggering step, and applying a polymerization step. In some embodiments, the triggering step includes application of electromagnetic energy of a first wavelength and intensity to the intraocular implant to cause photoisomerization of the masking compound. In some embodiments, polymerization step includes application of electromagnetic energy of a second wavelength and intensity to the intraocular implant to cause polymerization of a prepolymer.

In some embodiments, the first wavelength is between about 1 and about 800 nm, such as, between about 200 and about 800 nm, between about 250 and about 600 nm, between about 300 and about 500 nm, between about 300 and about 400 nm, between about 340 and about 365 nm (e.g., about 365 nm), or between about 340 and about 350 nm. For example, the first wavelength is less than 800 nm, or less than 600 nm, or less than 400 nm, or less than 365 nm. Also for example, the first wavelength is greater than 1 nm, or greater than 200 nm, or greater than 250 nm, or greater than 300 nm, or greater than 340 nm. In some embodiments, the second wavelength is between about 1 and about 800 nm, such as, between about 200 and about 800 nm, between about 300 and about 650 nm, between about 300 and about 500 nm, between about 300 and about 400 nm, between about 340 and about 370 nm (e.g., about 365 nm), or between about 340 and about 350 nm. For example, the second wavelength is less than 800 nm, or less than 600 nm, or less than 400 nm, or less than 365 nm. Also for example, the second wavelength is greater than 1 nm, or greater than 200 nm, or greater than 250 nm, or greater than 300 nm, or greater than 340 nm. In some embodiments, the first wavelength is about 340 to about 365 nm (e.g., about 350 nm), and the second wavelength is about 365 nm to about 400 nm. In some embodiments, the first and second wavelengths are the same or substantially overlapping ranges. In some embodiments, the first and second wavelengths are applied concurrently from the same light source.

In some embodiments, the application of a triggering and/or polymerization condition may be using a monochromatic source, such as filtered light, diffraction grating separated light or laser light. In some embodiments, the triggering and polymerization conditions are selected such the eye of the subject is not exposed to damaging high energy UV light. In some embodiments, the triggering and polymerization conditions are applied concurrently by application of light from the same light source.

In some embodiments, the method further includes waiting for a period of time sufficient to allow the masking compound to isomerize from the second isomer to the first isomer (e.g., reversible photoisomerization); and repeating the triggering step and the polymerization step. By period of time sufficient to allow the masking compound to isomerize from the second isomer to the first isomer is meant a period of time of about 1 minute or more, such as about 2 minutes or more, about 5 minutes or more, about 10 minutes or more, about 15 minutes or more, about 20 minutes or more, about 30 minutes or more, about 60 minutes or more, about 2 hours or more, about 3 hours or more, about 4 hours or more, about 5 hours or more, about 6 hours or more, about 12 hours or more, about 1 day or more, or even more. In some embodiments, the triggering and polymerization steps may be repeated multiple times, such as 2 times or more, 3 times or more, 4 times or more, 5 times or more, or even more.

In some embodiments, the method further includes determining the optical power of the lens and the eye of the subject and selecting the polymerization condition to produce a desirable change in the optical power of the implanted lens.

Aspects of the disclosure include methods of preparing the subject compositions and lenses. In some embodiments, the subject lens preparation method includes combining a matrix material, a masking compound, and a prepolymer.

Utility

The subject compositions and lenses described herein find use in a variety of applications, including but not limited to, ophthalmic devices and intraocular lenses for corrective eye surgery applications, materials applications such as color-changing materials (e.g., sunglasses, safety glasses, etc.), onlays, piggyback lenses and contact lenses. In some embodiments, the subject lenses of are used as intraocular implants, such as lenses that are used to treat vision disorders such as, myopia (nearsightedness), hyperopia (e.g., farsightedness, longsightedness or hypermetropia) and astigmatism. In some embodiments, the subject lenses may be used to treat cataracts, such as senile, morgagnian, secondary, traumatic or congenital cataracts.

Intraocular lenses can be inserted into various locations of the eye and used to supplement or correct the vision provided by the natural crystalline lens of the eye or can replace the natural crystalline lens of the eye. Lenses that supplement or correct the vision without replacing the natural crystalline lens are typically referred to as Phakic Lenses while lenses that replace the natural crystalline lens are typically referred to as Aphakic lenses. Phakic lenses can be located within the anterior chamber (AC) of the eye (AC Phakic lenses) or the posterior chamber (PC) of the eye (PC Phakic Lenses).

In some embodiments, the subject compositions find use in materials applications, e.g., applications where controlled modification of a material on demand is desired, such as but not limited to, optical coatings, transparent materials, electronic applications, inks, and the like. In such materials, polymerization of a prepolymer of the subject composition can be controlled on demand, as described herein, to produce a modified material. For example, the subject composition is stable to ambient condition (e.g., sunlight) until subjected to a triggering condition. In some embodiments, the modified material has a desirable property over the starting composition (e.g., an optical property, increased thickness or increased strength). In some embodiments, the subject compositions find use as color-changing materials, such as in sunglasses or lab safety glasses that may block a range of wavelengths of light. For example, in such applications, the subject compositions may provide a large color change upon application of light, that could be used as an indicator of how much light of selected wavelengths and intensities is applied.

EXAMPLES

Example 1

Solutions of MA, 1,4-butanediol diacrylate (BDDA), IC-651, and trans-azobenezene (t-AB) were prepared with varying ratios of IC-651 (2,2-dimethoxy-1,2-diphenylethan-1-one, Irgacure 651, Ciba Specialty Chemicals) and t-AB. The solutions were exposed to ambient sunlight to determine the time required for a crosslinked gel to form. For solutions having specific ratios of IC-651 and t-AB, no gel formation was observed after 14 days of exposure to sunlight. In these systems, sufficient amounts of t-AB were present such that the majority of the incident light was absorbed by the t-AB and the IC-651 was not able to initiate. Although absorption of sunlight may have caused some photoisomerization of the AB chromophores, thermal relaxation of the c-AB back to the t-AB maintained an equilibrium amount of these species in solution. To initiate polymerization, the solutions were irradiated using 350 nm light which effectively isomerized enough t-AB to cis-azobenzene (c-AB) and shifted the absorption maxima away from that of the IC-651, ultimately resulting in activation of the photoinitiator and polymerization of the MA/BDDA solution.

Example Type A: Photoinitiated polymerization of a liquid solution of methyl acrylate (MA) using Irgacure 651 (IC-651) as a photoinitiator was performed "on-demand" by using a photoisomerizable azobenzene (AB) UV-Vis absorber that allowed photoinitiation to occur only upon exposure to a specific light source. The absorbing AB dye inhibited photoinitiation in ambient sunlight for several days. Triggering photoinitiated polymerization was achieved by irradiation of solutions containing MA, AB, and IC-651 with 350 nm light which first isomerized trans-AB (t-AB) chromophores to cis-isomers (c-AB), significantly reducing the UV absorption overlap between this species and the IC-651. Thus, the photoisomerization and subsequent photoinitiated polymerization were performed under controlled conditions and premature initiation due to ambient light was avoided.

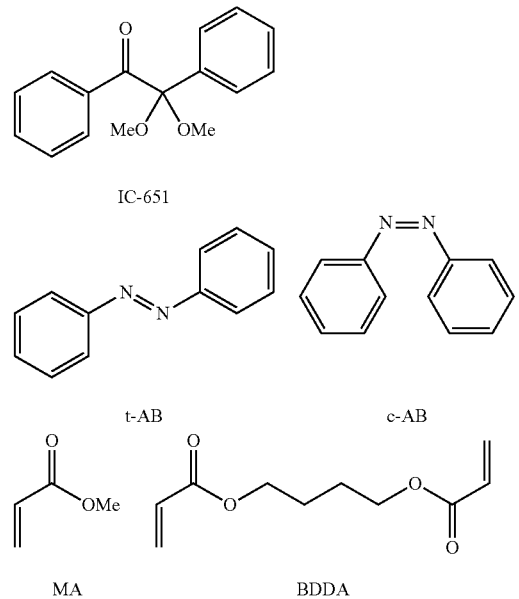

Solutions of MA, 1,4-butanediol diacrylate (BDDA), IC-651, and t-AB were prepared with varying ratios of IC-651 and t-AB. The solutions were exposed to ambient sunlight to determine the time required for a crosslinked gel to form. For solutions having specific ratios of IC-651 and t-AB, no gel formation was observed after 14 days of exposure to sunlight. In these systems, sufficient amounts of t-AB were present such that the majority of the incident light was absorbed by the t-AB and the IC-651 was not able to initiate. Although absorption of sunlight may have caused some photoisomerization of the AB chromophores, thermal relaxation of the c-AB back to the t-AB presumably maintained and equilibrium amount of these species in solution. To initiate polymerization, the solutions were irradiate using 350 nm light which effectively isomerized enough t-AB to c-AB and shifted the absorption maxima away from that of the IC-651, ultimately resulting in activation of the photoinitiator and polymerization of the MA/BDDA solution.

Experimental: Methyl acrylate and 1,4-butanediol diacrylate were each filtered through a column of activated alumina prior to use. A Pyrex vial was charged with methyl acrylate and 1,4-butanediol diacrylate. Azobenzene was added, followed by IC-651. The solution was divided into two separate Pyrex vials and each was sealed with a Teflon-lined screw cap. One vial was placed in direct sunlight and the other used for irradiation in a Luzchem photoreactor.

Example 2

Example Type B: A series of polysiloxane slabs were prepared that contained the aforementioned AB and IC-651 so that the photoinitiation would again be controllable "on-demand" upon exposure to a specified light source. The slabs also included Silicon MED 6820, Pt-divinyltetramethyldisiloxane complex, methacrylate-terminated telechelic dimethylsiloxane-co-diphenysiloxane polymer having $M_n$ of 7-10 kDa. The materials were combined as described below, degassed, and poured into stainless steel molds. The molded mixtures were then held in a Carver press at 1000 psi and 37° C. for 24-48 h. The slabs were then irradiated using laser light, while control slabs were exposed only to sunlight for a period of several days. Overall, certain compositions were found to withstand sunlight without signs of photoinitiated polymerization, whereas rapid photoinitiation was observed upon irradiation with 365 nm laser light even at relatively low power intensities.

Experimental: A mixture of Silicon MED 6820, Pt-divinyltetramethyldisiloxane complex, methacrylate-terminated telechelic dimethylsiloxane-co-diphenysiloxane polymer having $M_n$ of 7-10 kDa, azobenzene, and Irgacure 651 was degassed, then poured into stainless steel molds measuring 1×1×0.1 cm and again degassed. The molds were then placed into a Carver press at 1000 psi and 37° C. for 24 h. Slabs were then irradiated as described above, while duplicate slabs were placed in direct sunlight for comparison.

"On-demand" photoinitiated polymerization was demonstrated by the use of mixtures containing IC-651 as a photoinitiator for MA and containing BDDA as a crosslinking agent. Solutions of MA containing IC-651 (0.1 wt %) polymerized within minutes upon exposure to sunlight. Lower loadings of IC-651 failed to give complete polymerization, and samples prepared under either $N_2$ or ambient atmosphere performed similarly. Addition of t-AB was found to significantly delay the gel time depending upon the relative amount of t-AB present; key data are summarized in Table 1. Very low loading of t-AB did not impede the initiation significantly (entry 1), and gel formation occurred in less than 24 h when exposed to sunlight. The amount of t-AB relative to IC-651 was gradually increased until solutions could withstand multiple days in direct sunlight without undergoing polymerization.

Once resistance to sunlight had been established, polymerization was initiated by photoisomerization of the t-AB and activation of the IC-651 using a photoreactor. The samples were prepared in Pyrex vials and irradiated in a Luzchem LZC-ORG photoreactor equipped with 10 LZC-UVA bulbs (output wavelength centered at 350 nm). Samples with low loadings of t-AB polymerized within a few hours of exposure (entries 1-4), whereas those with at least a 100:1 ratio of t-AB to IC-651 failed to polymerize after 10 h of irradiation. An exemplary working condition included 0.1 wt % loading of IC-651 with 1.0 wt % loading of t-AB (entry 4). This sample withstood polymerization in sunlight for greater than 14 days, but was readily polymerized within 3 h upon exposure to 350 nm light in the photoreactor.

TABLE 1

Gel times required for samples exposed to sunlight or 350 nm light.[1]

| | Loading (wt %)[2] | | Gel Times[3] | |
|---|---|---|---|---|
| Entry | AB | IC-651 | Ambient (d) | Irradiated (h) |
| 1 | 0.001 | 0.1 | <1 | <1 |
| 2 | 0.01 | 0.1 | 3 | <1 |
| 3 | 0.1 | 0.1 | 10 | 1 |
| 4 | 1.00 | 0.1 | >14 | 3 |
| 5 | 10 | 0.1 | >14 | >10 |
| 6 | 20 | 0.1 | >14 | >10 |
| 7 | 30 | 0.1 | >14 | >10 |

[1]Reactions were conducted in Pyrex vials sealed under ambient atmosphere using methyl acrylate and 1,4-butanediol diacrylate each filtered through activated alumina gel prior to use.
[2]Solutions were prepared using methyl acrylate containing 5 wt % of 1,4-butanediol diacrylate and the indicated amounts of AB and IC-651.
[3]Solutions monitored under ambient light were placed outdoors in direct sunlight.

Slabs were next investigated as model systems for light-adjustable lenses. The slabs were irradiated at 365 nm using a 5.6 mm beam and an average irradiance of 12 mW/cm² (2.96 mW output power). Each slab was irradiated in four different locations with exposure times ranging from 30-120 s. Identical slabs were also placed outdoors for exposure to sunlight. All slabs were examined using interferometry to determine if photoinitiated polymerization and crosslinking had taken place. Slabs containing the AB molecules resisted polymerization in sunlight for several days. Irradiation using the 365 nm light source resulted in isomerization of the AB as described above and allowed photoinitiation and polymerization to occur. In this way, using low power densities for the controlled irradiation was successful in slabs that fully resisted polymerization in sunlight.

Example 3

Masking Compound Synthesis

The azobenzene compounds 1-5 and the triazine 6 (see structures below) were synthesized using standard synthetic methods. Compounds 1-5 were prepared to include dialkenes to facilitate the inclusion of the compound into a lens matrix upon polymerization. The synthetic methods are used to prepare azobenzene compounds that include both electron-donating and electron-withdrawing groups, in order to tune the spectral properties of the compounds.

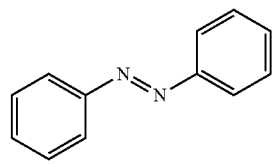

azobenzene

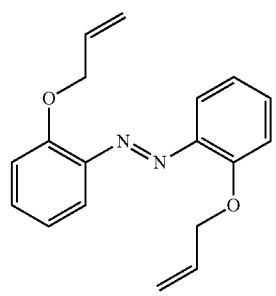

1

-continued

2

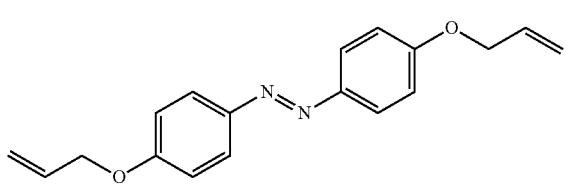

3

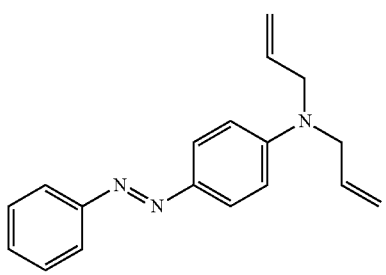

4

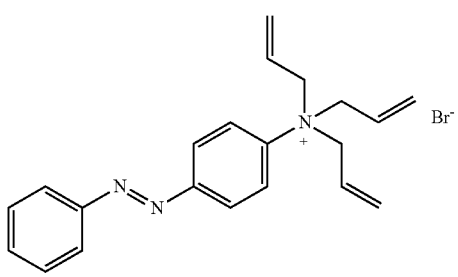

5

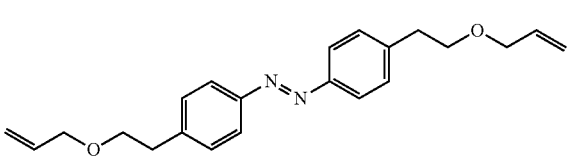

6

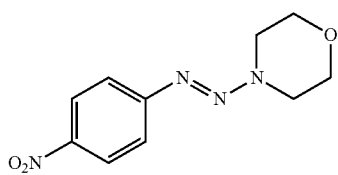

UV-Vis Spectroscopy

Figure 2:
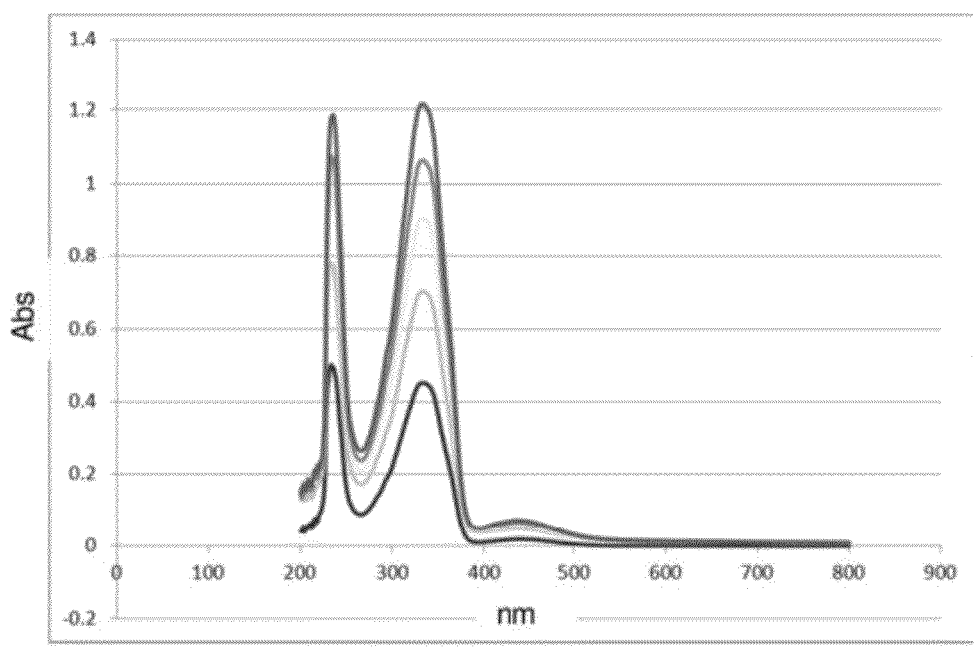
FIG. 2 shows the UV-vis spectra of solutions of an exemplary masking compound 5, as provided in Example 3, below. The five absorption curves correspond to those obtained from Solutions A through E, as described in Table 2.

Compound 5 was characterized using UV-vis spectroscopy, using the solutions of the dilution series shown in Table 2 below, and found to have $\lambda_{max}$=339 nm and $\epsilon$=29114 $M^{-1}$ $cm^{-1}$. See FIG. 2 for absorption spectra.

TABLE 2

| Solution | Stock Solution (1) | Stock [Azo] (M) | DCM | [Azo] (M) | 448 nm | 339 nm | 235 nm |
|---|---|---|---|---|---|---|---|
| A | 0.0001 | 1.00E-04 | 0.0009 | 0.00001 | 0.018 | 0.443 | 0.492 |
| B | 0.0002 | 1.00E-04 | 0.0009 | 1.81818E-05 | 0.048 | 0.693 | 0.774 |
| C | 0.0003 | 1.00E-04 | 0.0009 | 0.000025 | 0.057 | 0.889 | 0.972 |
| D | 0.0004 | 1.00E-04 | 0.0009 | 3.07692E-05 | 0.064 | 1.048 | 1.069 |
| E | 0.0005 | 1.00E-04 | 0.0009 | 3.57143E-05 | 0.071 | 1.196 | 1.186 |

Ambient Condition and Lab Testing

The compounds were evaluated by inclusion of the compounds into cross-linked poly(dimethylsiloxane) (PDMS) slabs at 0.2% by weight. The slabs also included a macromonomer, Irgacure 651 photoinitiator and Pt catalyst for hydrosilylation. The slabs were then exposed to sunlight for 24 hours, and evaluated colorimetrically.

Figure 3:
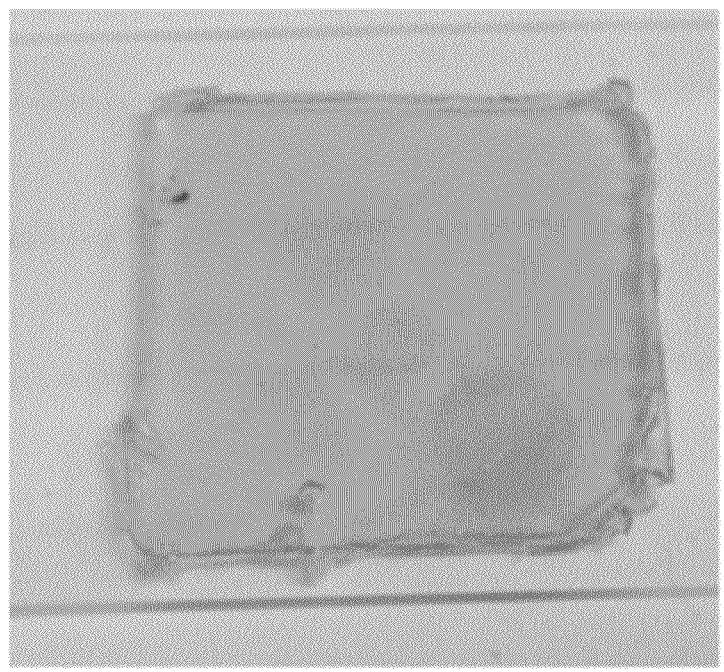
FIG. 3 illustrates an image of a slab containing an exemplary masking compound 5 that was subjected to a circular pattern of 365 nm light.

The slab containing compound 5 was subjected to 365 nm light in a concentric circle pattern for up to 10 minutes. Visual inspection of the slab (see FIG. 3) showed a dark coloration corresponding to the locations of the concentric circle pattern from application of 365 nm light. The image in FIG. 3, clearly shows the largest circle, and upon close inspection, shows further adjacent circle features corresponding to the pattern. The compound 5 containing slabs showed decreased initiation of the Irgacure compared to control slabs without the masking compound.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for modifying a composition, the method comprising:
   (a) a triggering step, comprising applying electromagnetic energy of a first wavelength and intensity to a pre-polymerized composition, wherein the triggering step causes photoisomerization of a masking compound in the composition; and
   (b) a polymerization or crosslinking step, comprising applying electromagnetic energy of a second wavelength and intensity to the photoisomerized composition, wherein the polymerization or crosslinking step causes polymerization or crosslinking of a prepolymer in the composition to form a polymerized composition;

wherein the photoisomerization converts the masking compound from a first photoisomer to a second photoisomer, and wherein the second photoisomer absorbs less light at the second wavelength than does the first photoisomer; and wherein the composition is an intraocular implant.

2. The method of claim 1, wherein the photoisomerization is selected from a cis-trans, cyclization, or ring-opening transition.

3. The method of claim 1, wherein the electromagnetic energy at the second wavelength induces polymerization by direct initiation of the prepolymer.

4. The method of claim 1, wherein the electromagnetic energy at the second wavelength induces polymerization indirectly on the prepolymer via activation of a photoinitiator.

5. The method of claim 1, wherein the electromagnetic energy at the second wavelength induces crosslinking of the prepolymer via a cross-linkable monomer or oligomer.

6. The method of claim 1, wherein the method further comprises:

(c) waiting for a period of time sufficient to allow the masking compound to isomerize from the second isomer to the first isomer; and (d) repeating the triggering step and the polymerization or crosslinking step.

7. The method of claim 1, wherein the polymerization or crosslinking step modifies an optical property of the implant.

8. The method of claim 1, wherein the masking compound is described by the structure of formula (I):

$$(Z^1)_{n1}-Y-(Z^2)_{n2} \quad (I)$$

wherein Y is a photoisomerizable moiety;

$n^1$ and $n^2$ are each independently 0, 1, 2 or 3; and each $Z^1$ and $Z^2$ is independently a polymerizable moiety or a crosslinking moiety that is connected to Y via an optional linker.

9. The method of claim 8, wherein Y is a photoisomerizable azoarylene, fulgide, spiropyran, naphthopyran, quinone, spirooxazine, nitrone, thioindigo, diarylethene, or dithienylethylene moiety.

10. The method of claim 8, wherein each $Z^1$ and $Z^2$ is independently a polymerizable or a crosslinking vinyl, vinylidene, diene, olefin, allyl, acrylate, acrylamide, or acrylic acid moiety.

11. The method of claim 8, wherein the optional linker is of 1 to 20 atoms in length.

12. The method of claim 8, wherein Y is a stilbene or azobenzene.

13. The method of claim 8, wherein the masking compound is described by the structure of formula (II):

(II)

where $n^3$ and $n^4$ are each independently 0, 1, 2, or 3;

each $Z^3$ and $Z^4$ is independently a polymerizable or crosslinking vinyl, vinylidene, diene, olefin, allyl, acrylate, acrylamide, or acrylic acid moiety;

$L^3$ and $L^4$ are independently linkers of 1 to 6 atoms in length;

$n^5$ and $n^6$ are each independently 0, 1, 2, 3, 4, or 5, provided that when $(Z^3)_{n3}$-$L^3$- is present, $n^5$ is not 5, and when -$L^4$-$(Z^4)_{n4}$ is present, $n^6$ is not 5; and each R is independently a hydrogen, alkyl, alkenyl, aryl, heterocycle, halogen, haloalkyl, perhaloalkyl, amino, hydroxyl, ether, nitro, cyano, carboxy, acyl, amido, ester, thio, thioether, sulfonyl, or sulfonamide.

14. The method of claim 8, wherein the masking compound is described by the structure of formula (III):

(III)

where $L^3$ and $L^4$ are independently —$(CH_2)_{m1}$—$Z^4$—$(CH_2)_{m2}$—;

$m^1$ and $m^2$ are each independently 0, 1, 2, 3, 4, 5, or 6;

$n^5$ and $n^6$ are each independently 0, 1, 2, 3, or 4;

$Z^4$ is a carbonyl, ester, amido, carbamate, sulfonyl, sulfonamide, ether, thioether, or urea moiety; and each R is independently a hydrogen, alkyl, alkenyl, aryl, heterocycle, halogen, haloalkyl, perhaloalkyl, amino, hydroxyl, ether, nitro, cyano, carboxy, acyl, amido, ester, thio, thioether, sulfonyl, or sulfonamide.

15. The method of claim 14, wherein the masking compound is described by the structure:

16. The method of claim 14, wherein $L^3$ and $L^4$ are —O— or —O—$(CH_2)_m$, where m is 1, 2, 3, 4, 5, or 6.

17. The method of claim 16, wherein $n^5$ and $n^6$ are both 0.

18. The method of claim 8, wherein the masking compound is described by the structure of formula (IV) or (V):

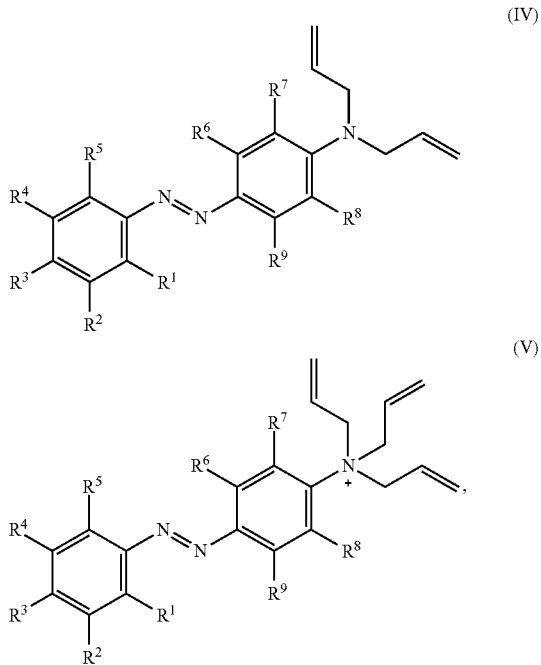

where $R^1$-$R^8$ are each independently hydrogen, hydrocarbyl, heterocycle, halogen, haloalkyl, perhaloalkyl, amino, hydroxyl, ether, nitro, cyano, carboxy, acyl, amido, ester, thiol, thioether, sulfonyl, or sulfonamide.

19. The method of claim 18, wherein at least one $R^1$-$R^8$ is -$L^5$-O—$CH_2CH$=$CH_2$, where $L^5$ is an optional linker group.

20. The method of claim 19, wherein each $L^5$ is a $C_1$-$C_6$ alkyl chain.

21. The method of claim 19, wherein each $L^5$ is absent.

22. The method of claim 18, wherein, $R^1$-$R^8$ are each hydrogen.

23. The method of claim 8, wherein the masking compound is described by the structure of formula (VI):

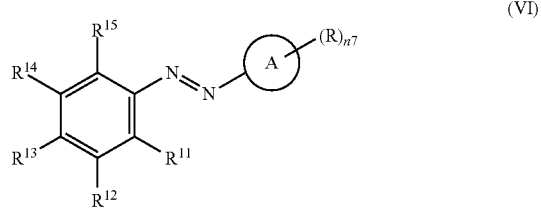

where,

A is a heterocycle ring;

$N^7$ is 0 or an integer from 1 to 5;

each R is independently hydrogen, -$L^5$-$(Z^5)_m$ where m is 1, 2 or 3, a hydrocarbyl, heterocycle, halogen, haloalkyl, perhaloalkyl, amino, hydroxyl, ether, nitro, cyano, carboxy, acyl, amido, ester, thiol, thioether, sulfonyl, or sulfonamide; and $R^{11}$-$R_{15}$ are each independently hydrogen, a hydrocarbyl, heterocycle, halogen, haloalkyl, perhaloalkyl, amino, hydroxyl, ether, nitro, cyano, carboxy, acyl, amido, ester, thiol, thioether, sulfonyl, sulfonamide, or -$L^5$-$Z^5$;

where $L^5$ is a linker and each $Z^5$ is independently a polymerizable group or a crosslinking group.

24. The method of claim 23, wherein A is a N-linked heterocycle of formula

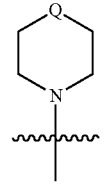

where Q is O or N-$R^{21}$, where $R^{21}$ is hydrogen, alkyl, aryl, acyl, heterocycle, or -$L^5$-$Z^5$.

25. The method of claim 24, wherein each $L^5$ is independently a $C_1$-$C_6$ alkyl chain.

26. The method of claim 24, wherein at least one of $R^{11}$-$R^{15}$ and $R^{21}$ comprises an allyl or a vinyl group.

27. The method of claim 24, wherein $R^{13}$ is —$(CH_2)_{m1}$-$L^6$-$(CH_2)_{m2}$—$Z^5$ where m1 and m2 are each independently 0 or an integer from 1 to 6, and $L^6$ is a carbonyl, ester, amido, carbamate, sulfonyl, sulfonamide, ether, a thioether, or urea group.

28. The method of claim 27, wherein m1 is 2 and m2 is 0.

29. The method of claim 27, wherein $L^6$ is —O—.

30. The method of claim 24, wherein at least one of $^{R11}$-$R^{15}$ and $R^{21}$ comprises -$L^7$-O—$CH_2CH$=$CH_2$, wherein $L^7$ is independently a $C_1$-$C_6$ alkyl chain.

31. The method of claim 24, wherein Q is O.

32. The method of claim 31, wherein at least one of $R^{11}$-$R^{15}$ is nitro.

33. The method of claim 32, wherein $R^{13}$ is nitro, and $R^{11}$, $R^{12}$, $R^{14}$ and $R^{15}$ are hydrogen.

34. The method of claim 8, wherein the masking compound is one of the following structures:

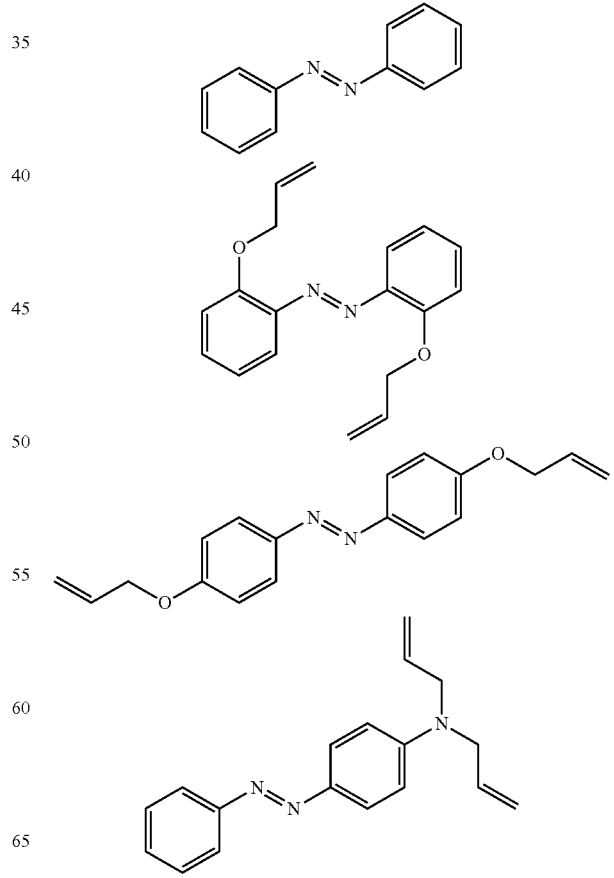

-continued

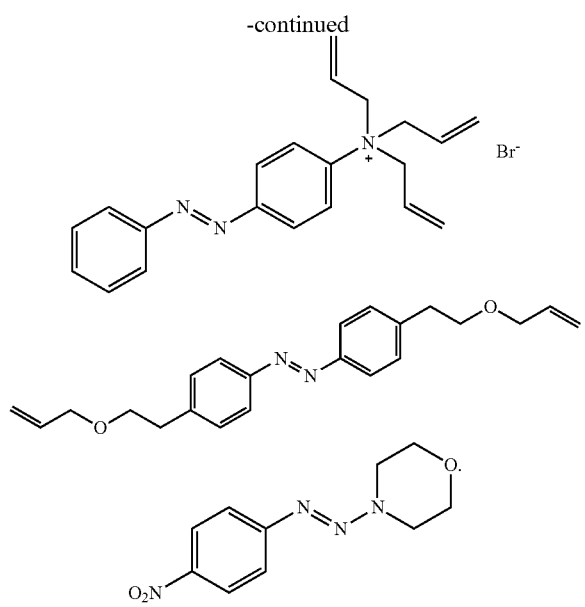

35. The method of claim 1, wherein the prepolymer comprises an acrylamide, acrylate, acrylonitrile, epoxy, methaacrylamide, methacrylate, unsaturated polyester, urethane, vinyl ester, or a combination thereof.

36. The method of claim 1, further comprises a photoinitiator.

37. The method of claim 1, wherein the steps of applying electromagnetic energy of the first and second wavelengths are performed concurrently.

38. The method of claim 1, wherein the electromagnetic energy of the first and second wavelengths is applied from the same light source.

39. The method of claim 1, wherein the first photoisomer of the masking compound is present in the composition before the polymerization or crosslinking step in a quantity sufficient to prevent polymerization or crosslinking of the prepolymer upon exposure of the pre-polymerized composition to ambient sunlight.

40. The method of claim 1, wherein the intraocular implant is inserted into an eye of a patient prior to the triggering and polymerizing or crosslinking steps.

* * * * *